United States Patent
Seetharaman et al.

(10) Patent No.: US 10,899,721 B2
(45) Date of Patent: Jan. 26, 2021

(54) TETRAZOLE BASED CORROSION INHIBITORS

(71) Applicant: ECOLAB USA INC., St. Paul, MN (US)

(72) Inventors: Jothibasu Seetharaman, Melpattampakkam (IN); Edouard Andre Reny, Oegstgeest (NL); Donald A. Johnson, Batavia, IL (US); Kailas B. Sawant, Aurora, IL (US); Vaideeswaran Sivaswamy, Pune (IN)

(73) Assignee: ECOLAB USA INC., St. Paul, MN (US)

( * ) Notice: Subject to any disclaimer, the term of this patent is extended or adjusted under 35 U.S.C. 154(b) by 0 days.

(21) Appl. No.: 15/676,086

(22) Filed: Aug. 14, 2017

(65) Prior Publication Data
US 2018/0009768 A1 Jan. 11, 2018

Related U.S. Application Data

(62) Division of application No. 14/557,737, filed on Dec. 2, 2014, now Pat. No. 9,771,336.

(60) Provisional application No. 61/910,833, filed on Dec. 2, 2013.

(51) Int. Cl.
*C07D 257/04* (2006.01)
*C09K 8/54* (2006.01)
*C23F 11/14* (2006.01)

(52) U.S. Cl.
CPC .............. *C07D 257/04* (2013.01); *C09K 8/54* (2013.01); *C23F 11/149* (2013.01)

(58) Field of Classification Search
CPC .................................................. C09K 2208/32
See application file for complete search history.

(56) References Cited

U.S. PATENT DOCUMENTS

| | | | | |
|---|---|---|---|---|
| 3,275,608 A * | 9/1966 | Montgomery | ....... | C07D 257/04 528/336 |
| 3,408,307 A * | 10/1968 | Troscinski | ............ | C23F 11/149 106/14.13 |
| 3,615,616 A | 10/1971 | Wilrijk et al. | | |
| 4,142,029 A * | 2/1979 | Illy | .......................... | C08J 9/108 521/95 |
| 4,758,312 A | 7/1988 | Hunt et al. | | |
| 5,082,611 A | 1/1992 | Adams et al. | | |
| 5,156,769 A | 10/1992 | Cha et al. | | |
| 5,746,947 A | 5/1998 | Vanderpool et al. | | |
| 5,874,026 A | 2/1999 | Pilsits, Jr. et al. | | |
| 6,379,587 B1 | 4/2002 | Chen | | |
| 6,572,789 B1 * | 6/2003 | Yang | ........................ | C02F 5/14 252/389.23 |
| 6,585,933 B1 * | 7/2003 | Ehrhardt | ................. | C23F 11/08 252/180 |
| 6,596,393 B1 * | 7/2003 | Houston | ............... | C23F 11/149 174/109 |
| 7,393,395 B2 | 7/2008 | Aiba et al. | | |
| 7,972,655 B2 | 7/2011 | Abys et al. | | |
| 8,025,840 B2 * | 9/2011 | Crovetto | ................. | C02F 5/105 422/17 |
| 2003/0063998 A1 | 4/2003 | Ghosh et al. | | |
| 2009/0101587 A1 * | 4/2009 | Blokker | .................... | C02F 5/14 210/701 |
| 2009/0104073 A1 * | 4/2009 | Kaiser | .................... | A01N 63/02 422/28 |
| 2010/0006796 A1 * | 1/2010 | Yang | ........................ | C09K 5/10 252/67 |
| 2010/0123100 A1 | 5/2010 | Gill et al. | | |

FOREIGN PATENT DOCUMENTS

| | | | |
|---|---|---|---|
| CN | 1359430 A | 7/2002 | |
| EP | 0462809 A1 | 12/1991 | |
| EP | 0454323 B1 * | 11/1995 | ............... C02F 5/14 |
| JP | 7-145491 | 6/1995 | |
| JP | 6-184771 | 7/1995 | |
| JP | 2002-543294 | 12/2002 | |
| JP | 2007-113078 | 5/2007 | |
| WO | WO 00/66810 A1 | 11/2000 | |
| WO | WO 2013/076509 A1 | 5/2013 | |

OTHER PUBLICATIONS

Finnegan et al. "An Improved Synthesis of 5-Substituted Tetrazoles" J. Am. Chem. Soc. 1958, 80, 3908-3911. (Year: 1958).*
Fürmeier et al. "Synthesis of New Heterocyclic Fatty Compounds" Eur. J. Org. Chem. 2003, 5, 885-893. (Year: 2003).*
Rodionov et al. "Benzimidazole and Related Ligands for Cu-Catalyzed Azide-Alkyne Cycloaddition" J. Am. Chem. Soc. 2007, 129, 12696-12704. (Year: 2007).*
Mansoori et al. "Thermally Stable Polymers Containing 1,3,4-Oxadiazole Units Obtained from Huisgen Reaction" Chin. J. Poly. Sci. 2012, 30, 36-44. (Year: 2012).*
Kauffman et al. "Metal hydrazides. XII. Synthesis of Diamidrazones from Aliphatic Dinitriles and Sodium Hydrazide." Chem. Ber. 1966, 99, 2600-2606. (Year: 1966).*
Partial Oral Translation of Chem. Ber. 1966, 8, 2600, at 2606, John Koytcheff, USPTO STIC Translation, Alexandria, VA (Apr. 7, 2020). (Year: 2020).*
Antonijevic, M.M. and M.B. Petrovic, "Copper Corrosion Inhibitors. A review," International Journal of Electrochemical Science, 3 (2008) pp. 1-28.

(Continued)

*Primary Examiner* — Amanda L. Aguirre
(74) *Attorney, Agent, or Firm* — Eric D. Babych; Barnes & Thornburg LLP

(57) ABSTRACT

Disclosed are corrosion inhibitor compounds and compositions useful for preventing or inhibiting corrosion of surfaces found in cooling water applications. In some embodiments, the surfaces may include mild steel, aluminum, brass, copper, galvanized steel, a copper alloy, admirality brass, or any combination thereof. Also disclosed are methods of using the compounds and compositions as corrosion inhibitors. In some embodiments, the corrosion inhibitor compounds and compositions are used in cooling water applications.

7 Claims, 12 Drawing Sheets

(56) References Cited

OTHER PUBLICATIONS

Brubaker, Carl H., Jr., "Metal Tetrazole Complexes: Bis-(5-aminotetrazolato)-copper(II)," Journal of the American Chemical Society, 82 (1960) pp. 82-85.

Finnegan, William G., R. A. Henry, and R. Lofquist, "An Improved Synthesis of 5-Substituted Tetrazoles," Journal of the American Chemical Society, 80 (1958) pp. 3908-3911.

Fürmeier, Sandra and J.O. Metzger, Synthesis of New Heterocyclic Fatty Compounds, European Journal of Organic Chemistry, (2003) pp. 885-893.

Kauffman, Thomas and L. Bán, "Synthese von Diamidrazonen aus aliphatischen Dinitrilen and Natriumhydrazid," Metallhydrazide XII, (1999) pp. 2600-2606, with English Abstract.

Liu, Pengju, X. Fang, Y. Tang, C. Sun, and C. Yao, "Electrochemical and Quantum Chemical Studies of 5-Substituted Tetrazoles as Corrosion Inhibitors for Copper in Aerated 0.5 M $H_2SO_4$ Solution," Materials Sciences and Applications, 2 (2011) pp. 1268-1278.

Nalco Chemical Company, Analytical Report, "Inhibitor AZ8104," Oct. 5, 1999, 2 pages.

Nalco Chemical Company, Analytical Report, "Inhibitor AZ8104," Oct. 19, 1999, 5 pages.

Nalco Chemical Company, Analytical Report, "10% As NaCITT—Research," Oct. 19, 1999, 5 pages.

Pillard, David A., J.S. Cornell, D.L. Dufresne, and M.T. Hernandez, "Toxicity of Benzotriazole and Benzotriazole Derivatives to Three Acquatic Species," Water Research, 35(2), (2001) pp. 557-560.

"Sebaconitrile," Chemical Book No. CB6371249 (Aug. 15, 2009) [database online]. Retrieved Dec. 19, 2016, from Chemical Book using Internet. http://www.chemicalbook.com/ChemicalProductProperty_EN_CB6371249.htm?CBNumber=CB6371249. 2 pages.

Sherif, El-Sayed M., "Electrochemical and Gravimetric Study on the Corrosion and Corrosion Inhibition of Pure Coper in Sodium Chloride Solutions by Two Azole Derivatives," International Journal of Electrochemical Science, 7 (2012), pp. 1482-1495.

International Search Report for PCT/US2014/068130, dated Mar. 20, 2015, 12 pages.

* cited by examiner

TETRAZOLE BASED CORROSION INHIBITORS

TECHNICAL FIELD

The present disclosure relates generally to corrosion inhibitors, and more particularly, the disclosure relates to tetrazole based corrosion inhibitor compounds and compositions.

BACKGROUND

Undesirable excess heat is removed in many industrial processes by the use of heat exchangers in which water is used as the heat exchange fluid. Copper and copper-bearing alloys are often used in the fabrication of such heat exchangers, as well as in other parts in contact with the cooling water, such as pump impellers, stators, and valve parts. The cooling fluid is often erosive and/or corrosive towards these metal parts by virtue of the cooling fluid having high turbidity, aggressive ions, and by the intentional introduction of oxidizing biocides for biological control.

The consequences of such erosion and corrosion are the loss of metal from the equipment, leading to failure or requiring expensive maintenance; creation of insoluble corrosion product films on the heat exchange surfaces, leading to decreased heat transfer and subsequent loss of productivity; and discharge of copper ions, which can then "plate out" on less noble metal surfaces and cause severe galvanic corrosion, a particularly insidious form of corrosion. Also, since copper is a toxic substance, its discharge to the environment is undesirable. Prevention or at least minimization of such discharge is a great problem in view of increasingly stringent public attitudes and legislation relating to pollution of the environment.

It is common practice to introduce corrosion inhibitors into the cooling water. These materials interact with the metal to directly produce a film that is resistant to corrosion, or to indirectly promote formation of protective films by activating the metal surface so as to form stable oxides or other insoluble salts. However, such films are not completely stable, but rather are constantly degrading under the influence of the aggressive conditions in the cooling water. Because of this effect, a constant supply of corrosion-inhibiting substances is generally maintained in the cooling water. A constant depletion of such substances occurs because many cooling systems are open, requiring continuous addition of fresh water to compensate for evaporation and blowdown (i.e., discharge). Continuous addition of fresh corrosion-inhibiting substances is likewise required so as to maintain, within defined limits, a concentration of such substances sufficient for the purpose of maintaining good corrosion inhibition. Moreover, currently used materials do not inhibit erosion of the copper-containing surfaces from the effects of particles in high turbidity water in many industrial processes.

Aromatic triazoles, namely tolyltriazole and benzotriazole, have been used for corrosion protection of yellow metals (e. g., copper and copper alloys) for several decades. However, tolyltriazole is generally preferred because of its lower cost. More recently, butylbenzotriazole and chlorotolyltriazole have also been used in industrial cooling water systems as disclosed, for example, in U.S. Pat. Nos. 4,744,950; 5,772,919 and 5,773,627.

Triazoles function as corrosion inhibitors by adsorbing to copper surfaces, thus providing a protective film that prevents both metal loss and oxygen reduction reactions. However, despite the fact that tolyltriazole and benzotriazole are among the most useful inhibitors for controlling yellow metal corrosion, the performance and cost-effectiveness of triazoles is limited by their consumption in aqueous systems.

The adsorption of triazoles to form protective films results in one form of triazole consumption, but with normal feed rates and metal surface area-to-system volume, this type of triazole loss is typically minimal.

Biodegradation is another known mechanism for the consumption of certain triazoles, such as the 5-methyl isomer of tolyltriazole. Triazoles can also be consumed by precipitation from solution with dissolved copper.

This is not considered a major contributing factor to triazole demand in typical applications, however, where copper is rarely in high enough concentrations to deplete the residual. Another major source of triazole consumption is due to reaction of triazoles with oxidizing halogens.

Many cooling water systems are treated with oxidizing halogens, such as chlorine gas, hypochlorite bleach, iodine/hypoiodous acid, chlorine dioxide, hypobromous acid, bromochloridimethylhydantoin, or stabilized versions of hypochlorous or hypobromous acids, to control microbiological growth. When yellow metals that have previously been protected with triazoles are exposed to an oxidizing halogen, corrosion protection breaks down. Many triazoles, including benzotriazole and tolyltriazole, are vulnerable to halogen attack. Very high dosages of triazoles are frequently added to cooling water systems in an attempt to form new protective films and improve performance.

Not only are triazoles consumed in cooling water systems treated with oxidizing halogens, but the halogens themselves are consumed as well. As the oxidizing halogen attacks the triazole, the halogen is consumed, thereby reducing its biocidal efficiency and reducing cost-performance of the biocide.

Other triazole consumption-related problems associated with combining triazoles and oxidizing halogens in aqueous systems include the formation of (1) volatile by-products which have an objectionable odor and can be released into the environment, (2) by-products that are less effective corrosion inhibitors and (3) toxic halogenated organics. The halogenated organics are particularly undesirable when waters from the aqueous systems are released into the environment, especially into a receiving body of water where toxicity to fish is a concern. Another problem is the inherent aggressiveness of the halogens towards the base metal.

Accordingly, it would be desirable to provide improved compounds, compositions, and methods of inhibiting corrosion of yellow metals in aqueous systems containing oxidizing halogens. It would also be desirable to utilize a corrosion inhibitor resistant to halogen attack and which does not interfere with the biocidal efficacy of the halogen. Furthermore, it would be desirable to provide corrosion inhibitors more environmentally friendly.

SUMMARY

In one aspect, disclosed is a composition for inhibiting corrosion at a surface, the composition comprising a tetrazole compound of formula (II),

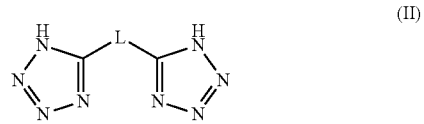
(II)

wherein,

L is $C_6$-$C_{10}$-alkylenyl, wherein said alkylenyl is substituted or unsubstituted with one or more suitable substituents.

In certain embodiments, L is $C_6$-$C_{10}$-alkylenyl substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl.

In certain embodiments, L is unsubstituted $C_6$-$C_{10}$-alkylenyl.

In certain embodiments, L is $C_6$-$C_{10}$-alkylenyl substituted with one, two, or three tetrazolyl groups, wherein said tetrazolyl groups are substituted or unsubstituted.

In certain embodiments, L is $C_6$-$C_{10}$-alkylenyl substituted with one, two, or three tetrazolyl groups, wherein said tetrazolyl groups are unsubstituted.

In certain embodiments, the compound of formula (II) is selected from the group consisting of: 1,6-di(1H-tetrazol-5-yl)hexane ("HDTZ"); 1,7-di(1H-tetrazol-5-yl)heptane ("HeDTZ"); 1,8-di(1H-tetrazol-5-yl)octane ("ODTZ"); and 5,5',5"-(hexane-1,3,6-triyl)tris(1H-tetrazole) ("TCH-TZ").

In certain embodiments, the composition further comprises one or more components, each component independently selected from the group consisting of: a solvent; a tracer; a scale inhibitor; a dispersant; an acid; and a base.

In certain embodiments, the composition comprises a solvent that is water.

In certain embodiments, the composition comprises about 40% by weight of one or more compounds of formula (II).

In certain embodiments, the composition has a pH of 6-12, a pH of 6-10, or a pH of 6-8. In certain embodiments, the composition has a pH of about 6, about 7, about 8, about 9, about 10, about 11, or about 12.

In certain embodiments, the composition is a stable water-based composition having a pH of 6-12, a pH of 6-10, or a pH of 6-8.

In certain embodiments, the composition inhibits corrosion at a surface that is a yellow metal surface. In certain embodiments, the composition inhibits corrosion at a surface that is a mild steel surface.

In another aspect, disclosed is a composition for inhibiting corrosion at a surface, the composition comprising: a tetrazole; a solvent; a tracer; a scale inhibitor; a dispersant; an acid; and a base.

In certain embodiments, the tetrazole is a compound of formula (II), as described above.

In certain embodiments, the tetrazole is a compound of formula (I),

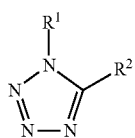

(I)

wherein,

R$^1$ and R$^2$ are each independently selected from the group consisting of hydrogen, alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl, wherein said alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl are each independently substituted or unsubstituted with one or more suitable substituents.

In certain embodiments, the tetrazole is a compound of formula (I), R$^1$ and R$^2$ are each independently selected from the group consisting of: hydrogen; $C_1$-$C_{10}$-alkyl; $C_2$-$C_{10}$-alkenyl; $C_2$-$C_{10}$-alkynyl; $C_6$-$C_{12}$-aryl; $C_6$-$C_{12}$-aryl-$C_1$-$C_{10}$-alkyl; $C_6$-$C_{12}$-aryl-$C_2$-$C_{10}$-alkenyl; $C_6$-$C_{12}$-aryl-$C_2$-$C_{10}$-alkynyl; five- or six-membered heteroaryl having one, two, three, or four heteroatoms independently selected from nitrogen, oxygen, and sulfur; heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; heteroaryl-$C_2$-$C_{10}$-alkynyl wherein the heteroaryl is a five- or six-membered heteroaryl having one, two, three, or four heteroatoms independently selected from nitrogen, oxygen, and sulfur; three-, four-, five-, six- or seven-membered heterocyclyl containing at least one heteroatom independently selected from nitrogen, oxygen, and sulfur; heterocyclyl-$C_1$-$C_{10}$-alkyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkenyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkynyl wherein the heterocyclyl is a three-, four-, five-, six- or seven-membered heterocyclic ring containing at least one heteroatom independently selected from nitrogen, oxygen, and sulfur; $C_3$-$C_8$-cycloalkyl; $C_3$-$C_8$-cycloalkyl-$C_1$-$C_{10}$-alkyl; $C_3$-$C_8$-cycloalkyl-$C_2$-$C_{10}$-alkenyl; and $C_3$-$C_8$-cycloalkyl-$C_2$-$C_{10}$-alkynyl; wherein said alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl are each independently substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl.

In certain embodiments, R$^1$ is hydrogen; and R$^2$ is tetrazolyl-$C_1$-$C_{10}$-alkyl, wherein the tetrazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl.

In certain embodiments, R$^1$ is hydrogen; and R$^2$ is tetrazolyl-$C_4$-alkyl, wherein the teterazolyl is unsubstituted. In certain embodiments, R$^1$ is hydrogen; and R$^2$ is tetrazolyl-$C_6$-$C_{10}$-alkyl, wherein the teterazolyl is unsubstituted.

In certain embodiments, R$^1$ is hydrogen; and R$^2$ is tetrazolyl-$C_6$-$C_{10}$-alkyl, wherein $C_6$-$C_{10}$-alkyl is further substituted with one, two, or three additional tetrazolyl groups.

In certain embodiments, the compound of formula (I) is selected from the group consisting of: 1,4-di(1H-tetrazol-5-yl)butane ("BDTZ"); 5-phenyl-1H-tetrazole ("PhTZ"); 1,2,3,4-tetrazole ("T"); 5-(p-tolyl)-1H-tetrazole ("TTZ"); 1,6-di(1H-tetrazol-5-yl)hexane ("HDTZ"); 1,7-di(1H-tetrazol-5-yl)heptane ("HeDTZ"); 1,8-di(1H-tetrazol-5-yl)octane ("ODTZ"); and 5,5',5"-(hexane-1,3,6-triyl)tris(1H-tetrazole) ("TCH-TZ").

In certain embodiments, the solvent is water.

In certain embodiments, the tracer is a fluorescent tracer.

In certain embodiments, the scale inhibitor is phosphinosuccinate oligomers (PSO).

In certain embodiments, the dispersant is a dispersant polymer

In certain embodiments, the acid is phosphoric acid.

In certain embodiments, the base is potassium hydroxide.

In certain embodiments, the composition comprises: 0.5 wt % to 3 wt % tetrazole; 25 wt % to 45 wt % water; 0.5 wt % to 1.5 wt % tracer; 2 wt % to 20 wt % scale inhibitor; 5 wt % to 25 wt % dispersant; 3 wt % to 7 wt % acid; and 5 wt % to 25 wt % base.

In certain embodiments, the composition comprises: 1.46 wt % tetrazole; 37.932 wt % water; 1 wt % tracer; 14.49 wt % of 31% PSO; 16.67 wt % of 45% dispersant polymer; 5.468 wt % of 85% $H_3PO_4$; and 22.98 wt % of 45% KOH.

In certain embodiments, the composition further comprises a triazole. The triazle may be selected from the group consisting of benzotriazole, tolyltriazole, butylbenzotriazole, halo-benzotriazoles, halo-tolyltriazoles, nitrated-triazoles, and combinations thereof.

In another aspect, disclosed is a method of inhibiting corrosion at a surface, the method comprising contacting the surface with a composition comprising a compound of formula (I) or formula (II).

In certain embodiments, the composition further comprises a solvent; a tracer; a scale inhibitor; a dispersant; an acid; and/or a base.

In certain embodiments, the surface is part of equipment used in the production, transportation, storage, and/or separation of crude oil or natural gas.

In certain embodiments, the surface is part of equipment used in a coal-fired process, a waste-water process, a farm, a slaughter house, a land-fill, a municipality waste-water plant, a coking coal process, or a biofuel process.

In certain embodiments, the surface is part of a cooling tower or cooling apparatus.

In certain embodiments, the surface comprises a yellow metal. In certain embodiments, the surface comprises a mild steel.

In another aspect, disclosed is a method of inhibiting corrosion of yellow metal surfaces in an aqueous system, wherein the aqueous system is treated with an oxidizing halogen, the method comprising adding an effective corrosion inhibiting amount of a composition to the aqueous system, wherein the composition comprises at least one tetrazole.

In certain embodiments, the tetrazole has formula (I) or formula (II).

In certain embodiments, the tetrazole is added to the aqueous system in an amount of from about 0.25 ppm to about 50 ppm or from about 0.1 ppm to about 20 ppm.

In certain embodiments, the aqueous system is contained within a cooling tower or cooling apparatus. In certain embodiments, the aqueous system is one in which some portion of the water is discharged into a water system containing at least one organism selected from fish, invertebrates, and algae.

In another aspect, disclosed is a method of inhibiting mild steel corrosion in an aqueous system, the method comprising adding an effective corrosion inhibiting amount of a composition to the aqueous system, wherein the composition comprises at least one tetrazole.

In certain embodiments, the tetrazole has formula (I) or formula (II).

In certain embodiments, the tetrazole is added to the aqueous system in an amount of from about 0.25 ppm to about 50 ppm or from about 0.1 ppm to about 20 ppm.

In certain embodiments, the aqueous system is contained within a cooling tower or cooling apparatus. In certain embodiments, the aqueous system is one in which some portion of the water is discharged into a water system containing at least one organism selected from fish, invertebrates, and algae.

In certain embodiments, the aqueous system comprises an oxidizing halogen, a copper (I) species, and/or a copper (II) species.

The compounds, compositions, methods and processes are further described herein.

DETAILED DESCRIPTION

Figure 1:
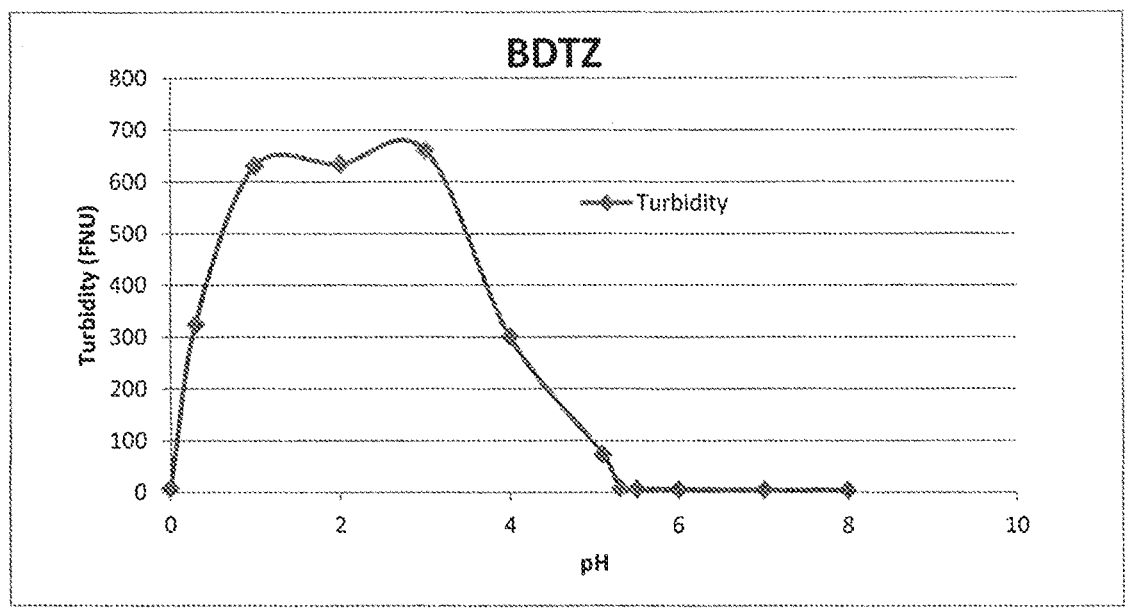
FIG. 1 depicts turbidity of 2% solutions of 1,4-di(1H-tetrazol-5-yl)butane ("BDTZ") versus pH.
Figure 2:
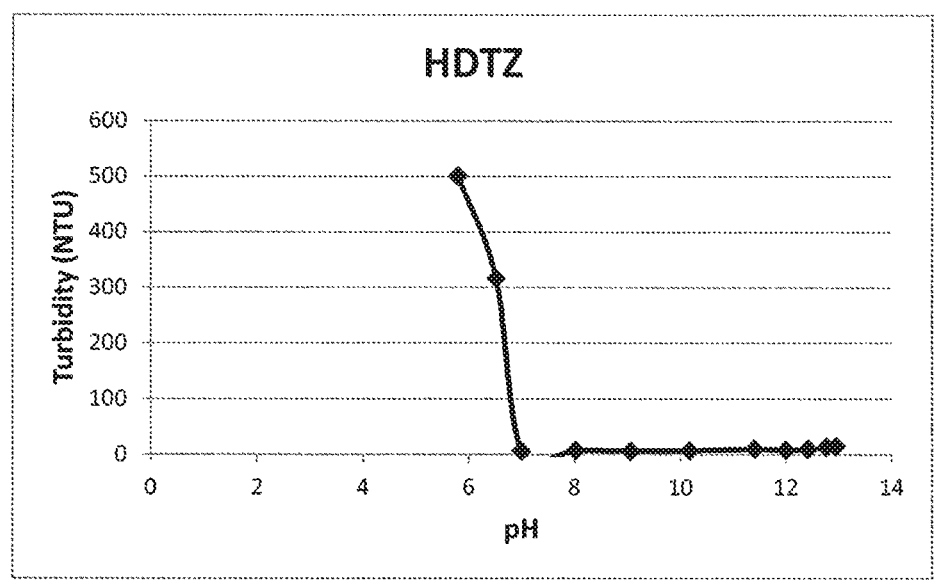
FIG. 2 depicts turbidity of 2% solutions of 1,6-di(1H-tetrazol-5-yl)hexane ("HDTZ") versus pH.
Figure 3:
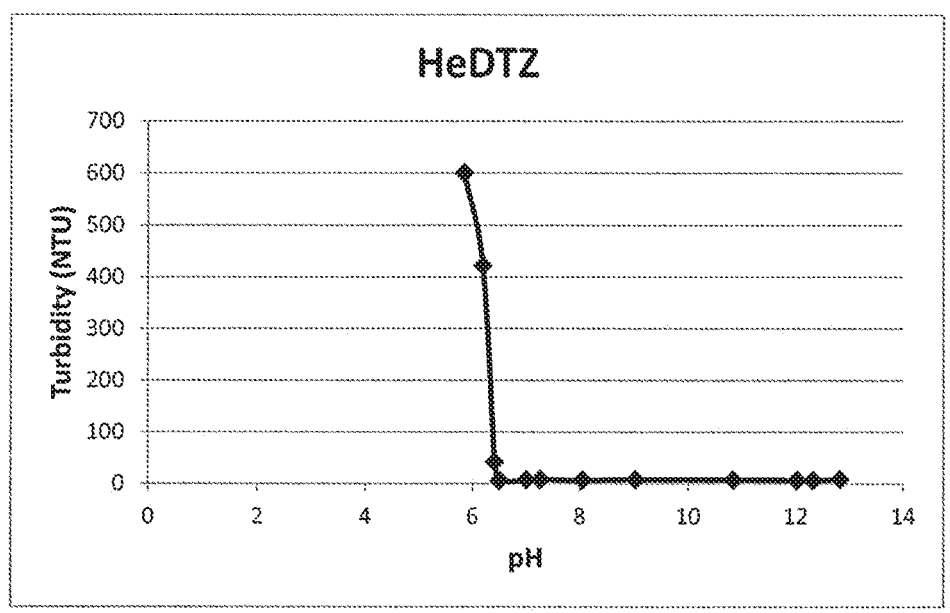
FIG. 3 depicts turbidity of 2% solutions of 1,7-di(1H-tetrazol-5-yl)heptane ("HeDTZ") versus pH.
Figure 4:
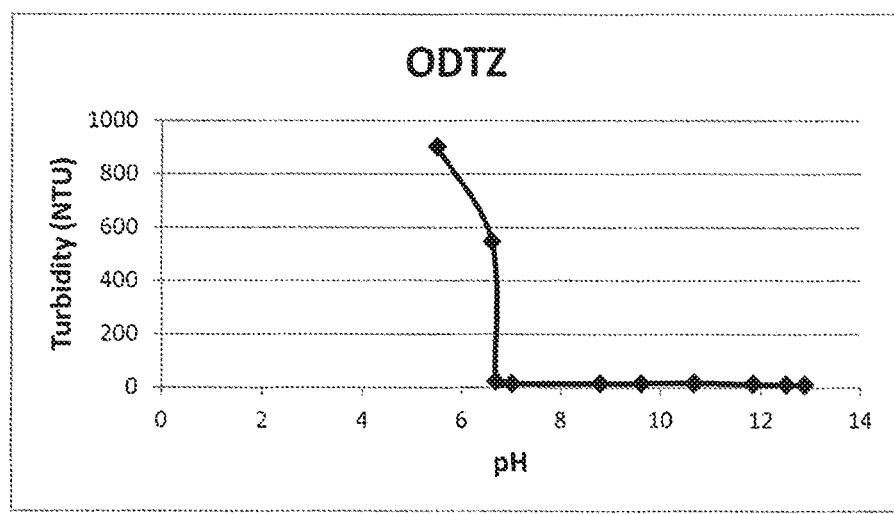
FIG. 4 depicts turbidity of 2% solutions of 1,8-di(1H-tetrazol-5-yl)octane ("ODTZ") versus pH.
Figure 5:
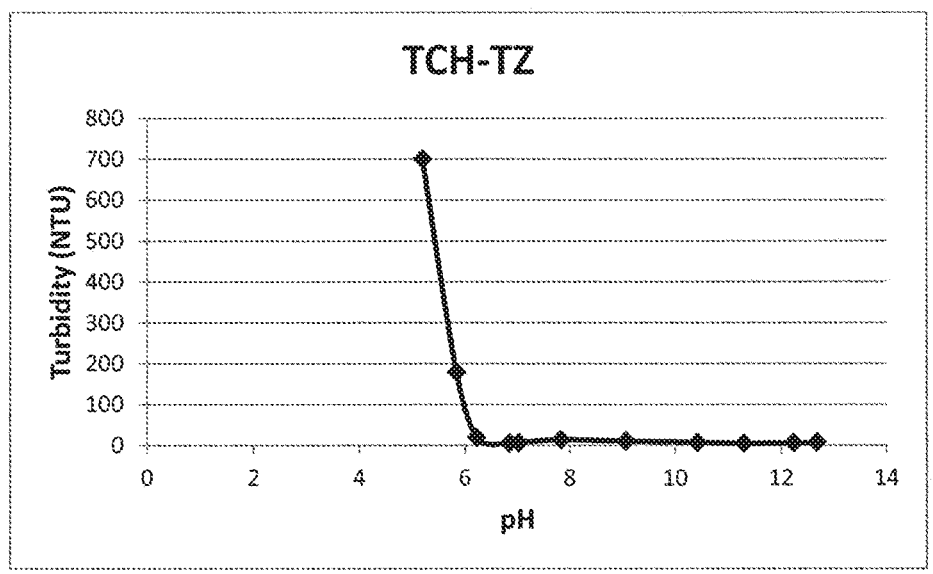
FIG. 5 depicts turbidity of 2% solutions of 5,5',5"-(hexane-1,3,6-triyl)tris(1H-tetrazole) ("TCH-TZ") versus pH.
Figure 6:
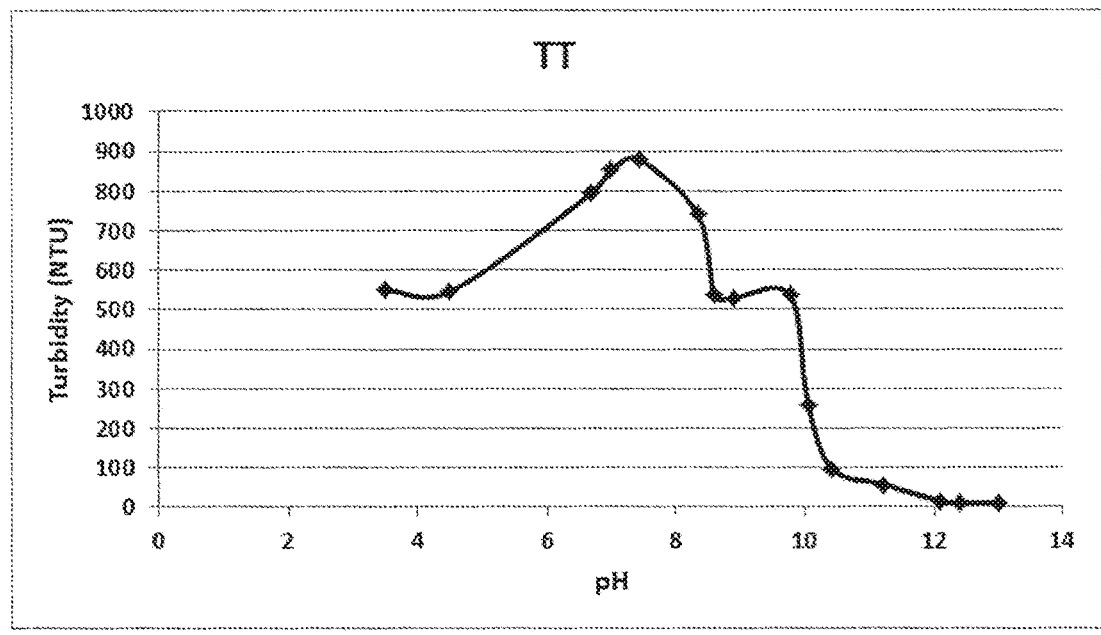
FIG. 6 depicts turbidity of 2% solutions of tolyltriazole ("TT") versus pH.

Disclosed herein are corrosion inhibitor compositions, methods of using the compositions, and processes for their preparation. The compositions are useful for inhibiting corrosion in cooling water applications. In particular, the compositions are useful for protecting yellow metals exposed to corrosive fluids. The compositions can be formulated at neutral pH, providing an improved environmental and safety profile compared to currently available products. The compositions can be provided with low toxicity profiles (acute and/or chronic), against for example, fish, invertebrates, algae, and mammals. The compositions are particularly useful for providing improved corrosion resistance for yellow metals exposed to halogens (e.g., via chlorination of cooling water). The compositions can also limit galvanic corrosion on mild steel (e.g., pitting attack), including when the steel is exposed to halogens (e.g., chlorination). The compositions may also exhibit a lower free chlorine demand compared to currently available corrosion inhibitors (e.g., triazoles, and triazole-based compositions).

1. DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, propyl (e.g., n-propyl, isopropyl), butyl (e.g., n-butyl, isobutyl, tert-butyl, sec-butyl), pentyl (e.g., n-pentyl, isopentyl, tert-pentyl, neopentyl, sec-pentyl, 3-pentyl), hexyl, heptyl, octyl, nonyl, and decyl. Alkyl groups may be unsubstituted or substituted by one or more suitable substituents, as defined above.

The term "alkylenyl" or "alkylene" as used herein, refers to a divalent group derived from a saturated, straight or branched hydrocarbon chain of from 1 to 32 carbon atoms. The term "$C_1$-$C_6$ alkylene" means those alkylene or alkylenyl groups having from 1 to 6 carbon atoms. Representative examples of alkylenyl groups include, but are not limited to, —$CH_2$—, —$CH(CH_3)$—, —$CH(C_2H_5)$—, —$CH(CH(CH_3)(C_2H_5))$—, —$C(H)(CH_3)CH_2CH_2$—, —$C(CH_3)_2$—, —$CH_2CH_2$—, —$CH_2CH_2CH_2$—, —$CH_2CH_2CH_2CH_2$—, and —$CH_2CH(CH_3)CH_2$—. Alkylenyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkenylenyl" or "alkenylene", as used herein, refers to a divalent group derived from a straight or branched chain hydrocarbon of 2 to 32 carbon atoms, which contains at least one carbon-carbon double bond. Representative examples of alkenylenyl groups include, but are not limited to, —C(H)=C(H)—, —C(H)=C(H)—$CH_2$—, —C(H)=C(H)—$CH_2$—$CH_2$—, —$CH_2$—C(H)=C(H)—$CH_2$—, —C(H)=C(H)—$CH(CH_3)$—, and —$CH_2$—C(H)=C(H)—$CH(CH_2CH_3)$—. Alkenylenyl groups may be unsubstituted or substituted by one or more suitable substituents, as defined above.

The term "alkynyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above.

The term "alkynylenyl" or "alkynylene", as used herein, refers to a divalent unsaturated hydrocarbon group which may be linear or branched and which has at least one carbon-carbon triple bond. Representative examples of alkynylenyl groups include, but are not limited to, —C≡C—, —C≡C—$CH_2$—, —C≡C—$CH_2$—$CH_2$—, —$CH_2$C≡C—$CH_2$—, —C≡C—$CH(CH_3)$—, and —$CH_2$—C≡C—$CH(CH_2CH_3)$—. Alkynylenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "arylalkyl," as used herein, refers to an aryl group attached to the parent molecular moiety through an alkyl group. Arylalkyl groups may be unsubstituted or substituted by one or more suitable substituents, as defined above.

The term "arylalkenyl," as used herein, refers to an aryl group attached to the parent molecular moiety through an alkenyl group. Arylalkenyl groups may be unsubstituted or substituted by one or more suitable substituents, as defined above.

The term "arylalkynyl," as used herein, refers to an aryl group attached to the parent molecular moiety through an alkynyl group. Arylalkynyl groups may be unsubstituted or substituted by one or more suitable substituents, as defined above.

The term "alkylarylalkyl," as used herein, refers to an alkylaryl group attached to the parent molecular moiety through an alkyl group. Alkylarylalkyl groups may be unsubstituted or substituted by one or more suitable substituents, as defined above.

The term "carbonyl," "(C=O)," or "—C(O)—" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "cycloalkylalkyl," as used herein, refers to a cycloalkyl group attached to the parent molecular moiety through an alkyl group. Cycloalkylalkyl groups may be unsubstituted or substituted by one or more suitable substituents, as defined above.

The term "alkylcycloalkylalkyl," as used herein, refers to a cycloalkylalkyl group substituted by one or more alkyl groups. Alkylcycloalkylalkyl groups may be unsubstituted or substituted by one or more suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 4 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heteroarylalkyl," as used herein, refers to a heteroaryl group attached to the parent molecular moiety through an alkyl group. Heteroarylalkyl groups may be unsubstituted or substituted by one or more suitable substituents, as defined above.

The term "alkylheteroarylalkyl," as used herein, refers to a heteroarylalkyl group substituted by one or more alkyl groups. Alkylheteroarylalkyl groups may be unsubstituted or substituted by one or more suitable substituents, as defined above.

The term "heterocycle" or "heterocyclyl," as used herein, refers to a monocyclic, bicyclic, or tricyclic group containing 1 to 4 heteroatoms selected from N, O, $S(O)_n$, $P(O)_n$, $PR^z$, NH or $NR^z$, wherein $R^z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "heterocyclylalkyl," as used herein, refers to a heterocycle group attached to the parent molecular moiety through an alkyl group. Heterocyclylalkyl groups may be unsubstituted or substituted by one or more suitable substituents, as defined above.

The term "alkylheterocyclylalkyl," as used herein refers to a heterocyclylalkyl group substituted by one or more alkyl groups. Alkylheterocyclylalkyl groups may be unsubstituted or substituted by one or more suitable substituents, as defined above.

The term "hydroxy," as used herein, refers to an —OH group.

The term "oxo," as used herein, refers to a double bonded oxygen (=O) radical wherein the bond partner is a carbon atom. Such a radical can also be thought as a carbonyl group.

The term "water cut," as used herein, means the percentage of water in a composition containing an oil and water mixture.

The term "$pH_{(i)}$," refers to initial pH.
The term "$pH_{(f)}$," refers to final pH.
The term "$FRC_i$," refers to initial free residual chlorine (ppm).
The term "$FRC_f$," refers to final free residual chlorine (ppm).
The term "$FRC_{MS}$," refers to material specific free residual chlorine demand.
The term "PSO," refers to phosphino succinic oligomer.
The term "HEDP," refers to 1-hydroxyethylidene-1,1-diphosphonic acid.
The term "T," may refer to 1H-tetrazole.
The term "TT," refers to 5-methyl-1H-benzotriazole.
The term "BZT," refers to 1H-benzotriazole.
The term "BBT," refers to 5-butyl-1H-benzotriazole.
The term "CITT," refers to 5-methyl-6-chloro-1H-benzotriazole.
The term "BDTZ," refers to 1,4-di(1H-tetrazol-5-yl)butane.
The term "HDTZ," refers to 1,6-di(1H-tetrazol-5-yl)hexane.
The term "TTZ," refers to 5-(p-tolyl)-1H-tetrazole.
The term "HTT," refers to hydrogenated tolyltriazole.
The term "PeDTZ," refers to 1,5-di(1H-tetrazol-5-yl)pentane.
The term "HeDTZ," refers to 1,7-di(1H-tetrazol-5-yl)heptane.
The term "ODTZ," refers to 1,8-di(1H-tetrazol-5-yl)octane.
The term "TCH-TZ," refers to 5,5',5"-(hexane-1,3,6-triyl)tris(1H-tetrazole).
The term "PhTZ," refers to 5-phenyl-1H-tetrazole.
The term "NMR," refers to nuclear magnetic resonance spectroscopy.

The term "MS," refers to mass spectrum.
The term "mpy," refers to mils per year.
The term "mmpy," refers to millimeters per year.
The term "ppm," refers to parts per million.
The term "RO," refers to reverse osmosis.
The term "mmol," refers to milli moles.
The term "KOH," refers to potassium hydroxide.
The term "HCl," refers to hydrochloric acid.
The term "H$_3$PO$_4$," ortho phosphoric acid.
The term "DMSO-d$_6$," refers to deuterated N,N'-dimethylsulfoxide.
The term "DPD," refers to N,N-diethyl-p-phenylenediamine.
The term "HPLC," refers to high performance liquid chromatography.
The term "OB," refers to oxidizing biocides.

2. COMPOSITIONS

The compositions disclosed herein include a tetrazole component. The compositions may further include one or more tracers, scale inhibitors, dispersants, acids, bases, and/or solvents. The compositions may further include additional corrosion inhibitors, asphaltene inhibitors, paraffin inhibitors, emulsifiers, water clarifiers, emulsion breakers, hydrogen sulfide scavengers, gas hydrate inhibitors, biocides, pH modifiers, surfactants, additional components, and combinations thereof.

The compositions are useful for protecting yellow metals exposed to corrosive fluids. The compositions can be formulated at neutral pH, providing an improved environmental and safety profile compared to currently available products. The compositions can be provided with low toxicity profiles (acute and/or chronic), against for example, fish, invertebrates, algae, and mammals. The compositions are particularly useful for providing improved corrosion resistance for yellow metals exposed to halogens (e.g., via chlorination of cooling water). The compositions can also limit galvanic corrosion on mild steel (e.g., pitting attach), including when the steel is exposed to halogens (e.g., chlorination). The compositions may also exhibit a lower free chlorine demand compared to currently available corrosion inhibitors (e.g., triazoles, and triazole-based compositions).

The compositions may provide corrosion protection in cooling water applications. The compositions may provide corrosion protection in applications relating to coal-based power plants. The compositions may provide corrosion protection in applications relating to the production, transportation, storage, and separation of crude oil and natural gas.

The compositions may include a tetrazole component, a base (e.g., NaOH), and water (e.g., reverse osmosis water). The compositions may include a tetrazole component, a solvent (e.g., water), a tracer, a scale inhibitor, a dispersant, an acid, and a base.

The compositions may have a pH of 6-12, a pH of 6-10, or a pH of 6-8. The compositions may have a pH of 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0. The compositions may have a pH of about 6, about 7, about 8, about 9, about 10, about 11, or about 12.

The compositions may inhibit corrosion at a metal surface, such as a mild steel surface. The compositions may also inhibit corrosion at a surface comprising brass, galvanized steel, aluminum, admirality brass, copper, copper alloys, or a combination thereof. The compositions may inhibit corrosion of a surface in contact with an aqueous system, such as the surfaces disclosed in this paragraph. The aqueous system may include one or more corrosive agents. The aqueous system may include an oxidizing agent. The aqueous system may include halogen species. The aqueous system may include an oxidizing, halogen-containing agent. The aqueous system may include one or more copper (I) species, and/or one or more copper (II) species.

The compositions may inhibit corrosion at a mild steel surface in contact with an aquous system including one or more copper (II) species. The compositions may inhibit mild steel corrosion by inactivating $Cu^{2+}$. The compositions may inactivate copper (II) by forming bis(tetrazolato)copper(II) monohydrate species.

The compositions may exhibit low toxicity to fish, invertebrates, algae, and other organisms. The compositions may exhibit low acute and/or low chronic toxicity to fish, invertebrates, algae, and other organisms. The compositions, against fish, invertebrates, algae, or other organisms, may exhibit a lethal concentration ($LD_{50}$) of 1,000 mg/L or greater, 2,000 mg/L or greater, 3,000 mg/L or greater, 4,000 mg/L or greater, 5,000 mg/L or greater, 6,000 mg/L or greater, 7,000 mg/L or greater, 8,000 mg/L or greater, 9,000 mg/L or greater, 10,000 mg/L or greater, 15,000 mg/L or greater, 20,000 mg/L or greater, 25,000 mg/L or greater, 30,000 mg/L or greater, 35,000 mg/L or greater, 40,000 mg/L or greater, 45,000 mg/L or greater, 50,000 mg/L or greater, or 100,000 mg/L or greater.

The compositions may provide a corrosion rate at a selected surface (e.g., a yellow metal surface or a mild steel surface) in a selected system (e.g., an aqueous system, such as in a cooling tower) of 0.1000 mils per year (mpy) or less, 0.0900 mpy or less, 0.0800 mpy or less, 0.0700 mpy or less, 0.0600 mpy or less, 0.0500 mpy or less, 0.0400 mpy or less, 0.0300 mpy or less, 0.0200 mpy or less, 0.0100 mpy or less, 0.0090 mpy or less, 0.0080 mpy or less, 0.0070 mpy or less, 0.0070 mpy or less, 0.0060 mpy or less, 0.0050 mpy or less, 0.0040 mpy or less, 0.0030 mpy or less, 0.0020 mpy or less, or 0.0010 mpy or less. The foregoing corrosion rates may include systems where the surface is exposed to oxidizing agents (e.g., bleach), and/or copper species (e.g., $Cu^{2+}$).

a. Tetrazole Component

The compositions disclosed herein include a tetrazole component. The tetrazole component may act as a corrosion inhibitor. The tetrazoles may be particularly useful for preventing and/or reducing corrosion in cooling water systems (e.g., cooling towers) and equipment used in the oil, gas, and/or coal industries (e.g., pipelines).

In one aspect, the tetrazole component is a compound of formula (I), or a salt thereof,

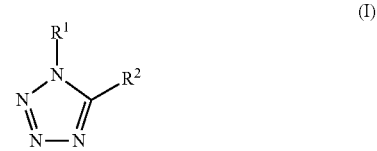

wherein,
$R^1$ and $R^2$ are each independently selected from the group consisting of hydrogen, alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl, wherein said alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl are each independently substituted or unsubstituted with one or more suitable substituents.

In certain embodiments, $R^1$ and $R^2$ are each independently selected from the group consisting of: hydrogen; $C_1$-$C_{10}$-alkyl; $C_2$-$C_{10}$-alkenyl; $C_2$-$C_{10}$-alkynyl; $C_6$-$C_{12}$-aryl; $C_6$-$C_{12}$-aryl-$C_1$-$C_{10}$-alkyl; $C_6$-$C_{12}$-aryl-$C_2$-$C_{10}$-alkenyl; $C_6$-$C_{12}$-aryl-$C_2$-$C_{10}$-alkynyl; five- or six-membered heteroaryl having one, two, three, or four heteroatoms independently selected from nitrogen, oxygen, and sulfur; heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; heteroaryl-$C_2$-$C_{10}$-alkynyl wherein the heteroaryl is a five- or six-membered heteroaryl having one, two, three, or four heteroatoms independently selected from nitrogen, oxygen, and sulfur; three-, four-, five-, six- or seven-membered heterocyclyl containing at least one heteroatom independently selected from nitrogen, oxygen, and sulfur; heterocyclyl-$C_1$-$C_{10}$-alkyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkenyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkynyl wherein the heterocyclyl is a three-, four-, five-, six- or seven-membered heterocyclic ring containing at least one heteroatom independently selected from nitrogen, oxygen, and sulfur; $C_3$-$C_8$-cycloalkyl; $C_3$-$C_8$-cycloalkyl-$C_1$-$C_{10}$-alkyl; $C_3$-$C_8$-cycloalkyl-$C_2$-$C_{10}$-alkenyl; and $C_3$-$C_8$-cycloalkyl-$C_2$-$C_{10}$-alkynyl; wherein said alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl are each independently substituted or unsubstituted with one or more suitable substituents.

In certain embodiments, $R^1$ and $R^2$ are each independently selected from the group consisting of: hydrogen; $C_1$-$C_{10}$-alkyl; $C_2$-$C_{10}$-alkenyl; $C_2$-$C_{10}$-alkynyl; $C_6$-$C_{12}$-aryl; $C_6$-$C_{12}$-aryl-$C_1$-$C_{10}$-alkyl; $C_6$-$C_{12}$-aryl-$C_2$-$C_{10}$-alkenyl; $C_6$-$C_{12}$-aryl-$C_2$-$C_{10}$-alkynyl; five- or six-membered heteroaryl having one, two, three, or four heteroatoms independently selected from nitrogen, oxygen, and sulfur; heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; heteroaryl-$C_2$-$C_{10}$-alkynyl wherein the heteroaryl is a five- or six-membered heteroaryl having one, two, three, or four heteroatoms independently selected from nitrogen, oxygen, and sulfur; three-, four-, five-, six- or seven-membered heterocyclyl containing at least one heteroatom independently selected from nitrogen, oxygen, and sulfur; heterocyclyl-$C_1$-$C_{10}$-alkyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkenyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkynyl wherein the heterocyclyl is a three-, four-, five-, six- or seven-membered heterocyclic ring containing at least one heteroatom independently selected from nitrogen, oxygen, and sulfur; $C_3$-$C_8$-cycloalkyl; $C_3$-$C_8$-cycloalkyl-$C_1$-$C_{10}$-alkyl; $C_3$-$C_8$-cycloalkyl-$C_2$-$C_{10}$-alkenyl; and $C_3$-$C_8$-cycloalkyl-$C_2$-$C_{10}$-alkynyl; wherein said alkyl, alkenyl, alkynyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, cycloalkyl, cycloalkylalkyl, cycloalkylalkenyl, and cycloalkylalkynyl are each independently substituted or unsubstituted with 1 to 3 substituents independently selected from the group consisting of —F, —Cl, —$NO_2$, —CN, —OH, —$NH_2$, $C_1$-$C_6$ alkyl, $C_1$-$C_6$ haloalkyl, $C_1$-$C_6$ alkoxy, —$CO_2R^3$, and —$CON(R^4)_2$, wherein $R^3$ and $R^4$, at each occurrence, are each independently selected from the group consisting of hydrogen and $C_1$-$C_6$ alkyl.

In certain embodiments, $R^1$ is hydrogen; and $R^2$ is selected from the group consisting of $C_6$-$C_{12}$-aryl-$C_1$-$C_{10}$-alkyl; $C_6$-$C_{12}$-aryl-$C_2$-$C_{10}$-alkenyl; $C_6$-$C_{12}$-aryl-$C_2$-$C_{10}$-alkynyl; heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; heteroaryl-$C_2$-$C_{10}$-alkynyl wherein the heteroaryl is a five- or six-membered heteroaryl having one, two, three, or four heteroatoms independently selected from nitrogen, oxygen, and sulfur; heterocyclyl-$C_1$-$C_{10}$-alkyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkenyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkynyl wherein the heterocyclyl is a three-, four-, five-, six- or seven-membered heterocyclic ring containing at least one heteroatom independently selected from nitrogen, oxygen, and sulfur; $C_3$-$C_8$-cycloalkyl-$C_1$-$C_{10}$-alkyl; $C_3$-$C_8$-cycloalkyl-$C_2$-$C_{10}$-alkenyl; and $C_3$-$C_8$-cycloalkyl-$C_2$-$C_{10}$-alkynyl; wherein said arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, cycloalkylalkyl, cycloalkylalkenyl, and cycloalkylalkynyl are each independently substituted or unsubstituted with one or more suitable substituents.

In certain embodiments, $R^1$ is hydrogen; and $R^2$ is selected from the group consisting of $C_6$-$C_{12}$-aryl-$C_1$-$C_{10}$-alkyl; $C_6$-$C_{12}$-aryl-$C_2$-$C_{10}$-alkenyl; $C_6$-$C_{12}$-aryl-$C_2$-$C_{10}$-alkynyl; heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; heteroaryl-$C_2$-$C_{10}$-alkynyl wherein the heteroaryl is a five- or six-membered heteroaryl having one, two, three, or four heteroatoms independently selected from nitrogen, oxygen, and sulfur; heterocyclyl-$C_1$-$C_{10}$-alkyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkenyl wherein the heterocyclyl is a three-, four-, five-, six- or seven-membered heterocyclic ring containing at least one heteroatom independently selected from nitrogen, oxygen, and sulfur; heterocyclyl-$C_2$-$C_{10}$-alkynyl wherein the heterocyclyl is a three-, four-, five-, six- or seven-membered heterocyclic ring containing at least one heteroatom independently selected from nitrogen, oxygen, and sulfur; $C_3$-$C_8$-cycloalkyl-$C_1$-$C_{10}$-alkyl; $C_3$-$C_8$-cycloalkyl-$C_2$-$C_{10}$-alkenyl; and $C_3$-$C_8$-cycloalkyl-$C_2$-$C_{10}$-alkynyl; wherein said arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, cycloalkylalkyl, cycloalkylalkenyl, and cycloalkylalkynyl are each independently substituted or unsubstituted with 1 to 3 substituents independently selected from the group consisting of —F, —Cl, —$NO_2$, —CN, —OH, —$NH_2$, $C_1$-$C_6$ alkyl, $C_1$-$C_6$ haloalkyl, $C_1$-$C_6$ alkoxy, —$CO_2R^3$, and —$CON(R^4)_2$, wherein $R^3$ and $R^4$, at each occurrence, are each independently selected from the group consisting of hydrogen and $C_1$-$C_6$ alkyl.

In certain embodiments, $R^1$ is hydrogen; and $R^2$ is selected from the group consisting of heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; and heteroaryl-$C_2$-$C_{10}$-alkynyl wherein the heteroaryl is a five- or six-membered heteroaryl having one, two, three, or four heteroatoms independently selected from nitrogen, oxygen, and sulfur; wherein said heteroarylalkyl, heteroarylalkenyl, and heteroarylalkynyl are each independently substituted or unsubstituted with one or more suitable substituents.

In certain embodiments, $R^1$ is hydrogen; and $R^2$ is selected from the group consisting of heteroaryl-$C_1$-$C_{10}$-alkyl wherein the heteroaryl is a five- or six-membered heteroaryl having one, two, three, or four heteroatoms independently selected from nitrogen, oxygen, and sulfur; heteroaryl-$C_2$-$C_{10}$-alkenyl wherein the heteroaryl is a five- or six-membered heteroaryl having one, two, three, or four heteroatoms independently selected from nitrogen, oxygen, and sulfur; and heteroaryl-$C_2$-$C_{10}$-alkynyl wherein the heteroaryl is a five- or six-membered heteroaryl having one, two, three, or four heteroatoms independently selected from nitrogen, oxygen, and sulfur; wherein said heteroarylalkyl, heteroarylalkenyl, and heteroarylalkynyl are each independently substituted or unsubstituted with 1 to 3 substituents independently selected from the group consisting of —F, —Cl, —$NO_2$, —CN, —OH, —$NH_2$, $C_1$-$C_6$ alkyl, $C_1$-$C_6$ haloalkyl, $C_1$-$C_6$ alkoxy, —$CO_2R^3$, and —$CON(R^4)_2$, wherein $R^3$ and $R^4$, at each occurrence, are each independently selected from the group consisting of hydrogen and $C_1$-$C_6$ alkyl.

In certain embodiments, $R^1$ is hydrogen; and $R^2$ is heteroaryl-$C_1$-$C_{10}$-alkyl wherein the heteroaryl is a five- or six-membered heteroaryl having one, two, three, or four heteroatoms independently selected from nitrogen, oxygen, and sulfur; wherein said heteroarylalkyl is substituted or unsubstituted with one or more suitable substituents.

In certain embodiments, $R^1$ is hydrogen; and $R^2$ is heteroaryl-$C_1$-$C_{10}$-alkyl wherein the heteroaryl is a five- or six-membered heteroaryl having one, two, three, or four heteroatoms independently selected from nitrogen, oxygen, and sulfur; wherein said heteroarylalkyl is substituted or unsubstituted with 1 to 3 substituents independently selected from the group consisting of —F, —Cl, —$NO_2$, —CN, —OH, —$NH_2$, $C_1$-$C_6$ alkyl, $C_1$-$C_6$ haloalkyl, $C_1$-$C_6$ alkoxy, —$CO_2R^3$, and —$CON(R^4)_2$, wherein $R^3$ and $R^4$, at each occurrence, are each independently selected from the group consisting of hydrogen and $C_1$-$C_6$ alkyl.

In certain embodiments, $R^1$ is hydrogen; and $R^2$ is tetrazolyl-$C_1$-$C_{10}$-alkyl, wherein the teterazolyl is substituted or unsubstituted with one or more suitable substituents. In certain embodiments, $R^1$ is hydrogen; and $R^2$ is tetrazolyl-$C_6$-$C_{10}$-alkyl, wherein the teterazolyl is substituted or unsubstituted with one or more suitable substituents.

In certain embodiments, $R^1$ is hydrogen; and $R^2$ is tetrazolyl-$C_1$-$C_{10}$-alkyl, wherein the tetrazolyl is substituted or unsubstituted with 1 to 3 substituents independently selected from the group consisting of —F, —Cl, —$NO_2$, —CN, —OH, —$NH_2$, $C_1$-$C_6$ alkyl, $C_1$-$C_6$ haloalkyl, $C_1$-$C_6$ alkoxy, —$CO_2R^3$, and —$CON(R^4)_2$, wherein $R^3$ and $R^4$, at each occurrence, are each independently selected from the group consisting of hydrogen and $C_1$-$C_6$ alkyl. In certain embodiments, $R^1$ is hydrogen; and $R^2$ is tetrazolyl-$C_6$-$C_{10}$-alkyl, wherein the tetrazolyl is substituted or unsubstituted with 1 to 3 substituents independently selected from the group consisting of —F, —Cl, —$NO_2$, —CN, —OH, —$NH_2$, $C_1$-$C_6$ alkyl, $C_1$-$C_6$ haloalkyl, $C_1$-$C_6$ alkoxy, —$CO_2R^3$, and —$CON(R^4)_2$, wherein $R^3$ and $R^4$, at each occurrence, are each independently selected from the group consisting of hydrogen and $C_1$-$C_6$ alkyl.

In certain embodiments, $R^1$ is hydrogen; and $R^2$ is tetrazolyl-$C_4$-alkyl, wherein the teterazolyl is substituted or unsubstituted with one or more suitable substituents. In certain embodiments, $R^1$ is hydrogen; and $R^2$ is tetrazolyl-$C_5$-alkyl, wherein the teterazolyl is substituted or unsubstituted with one or more suitable substituents. In certain embodiments, $R^1$ is hydrogen; and $R^2$ is tetrazolyl-$C_6$-alkyl, wherein the teterazolyl is substituted or unsubstituted with one or more suitable substituents. In certain embodiments, $R^1$ is hydrogen; and $R^2$ is tetrazolyl-$C_7$-alkyl, wherein the teterazolyl is substituted or unsubstituted with one or more suitable substituents. In certain embodiments, $R^1$ is hydrogen; and $R^2$ is tetrazolyl-$C_8$-alkyl, wherein the teterazolyl is substituted or unsubstituted with one or more suitable substituents. In certain embodiments, $R^1$ is hydrogen; and $R^2$ is tetrazolyl-$C_9$-alkyl, wherein the teterazolyl is substituted or unsubstituted with one or more suitable substituents. In certain embodiments, $R^1$ is hydrogen; and $R^2$ is tetrazolyl-$C_{10}$-alkyl, wherein the teterazolyl is substituted or unsubstituted with one or more suitable substituents.

In certain embodiments, $R^1$ is hydrogen; and $R^2$ is $C_1$-$C_{10}$-alkyl or $C_6$-$C_{10}$-alkyl, substituted with one, two, three, or four tetrazolyl groups, wherein each teterazolyl is independently substituted or unsubstituted with one or more suitable substituents. In certain embodiments, $R^1$ is hydrogen; and $R^2$ is $C_1$-$C_{10}$-alkyl or $C_6$-$C_{10}$-alkyl, substituted with two, three, or four tetrazolyl groups, wherein each tetrazolyl is independently substituted or unsubstituted with one or more suitable substituents. In certain embodiments, $R^1$ is hydrogen; and $R^2$ is $C_1$-$C_{10}$-alkyl or $C_6$-$C_{10}$-alkyl, substituted with two tetrazolyl groups, wherein each teterazolyl is independently substituted or unsubstituted with one or more suitable substituents. In certain embodiments, each tetrazolyl group is unsubstituted.

In certain embodiments, $R^1$ is hydrogen; and $R^2$ is tetrazolyl-$C_4$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, $R^1$ is hydrogen; and $R^2$ is tetrazolyl-$C_5$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, $R^1$ is hydrogen; and $R^2$ is tetrazolyl-$C_6$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, $R^1$ is hydrogen; and $R^2$ is tetrazolyl-$C_7$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, $R^1$ is hydrogen; and $R^2$ is tetrazolyl-$C_8$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, $R^1$ is hydrogen; and $R^2$ is tetrazolyl-$C_9$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, $R^1$ is hydrogen; and $R^2$ is tetrazolyl-$C_{10}$-alkyl, wherein the teterazolyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl.

In certain embodiments, $R^1$ is hydrogen; and $R^2$ is tetrazolyl-$C_4$-alkyl, wherein the teterazolyl is unsubstituted. In certain embodiments, $R^1$ is hydrogen; and $R^2$ is tetrazolyl-$C_5$-alkyl, wherein the teterazolyl is unsubstituted. In certain embodiments, $R^1$ is hydrogen; and $R^2$ is tetrazolyl-$C_6$-alkyl, wherein the teterazolyl is unsubstituted. In certain embodiments, $R^1$ is hydrogen; and $R^2$ is tetrazolyl-$C_7$-alkyl, wherein the teterazolyl is unsubstituted. In certain embodiments, $R^1$ is hydrogen; and $R^2$ is tetrazolyl-$C_8$-alkyl, wherein the teterazolyl is unsubstituted. In certain embodiments, $R^1$ is hydrogen; and $R^2$ is tetrazolyl-$C_9$-alkyl, wherein the teterazolyl is unsubstituted. In certain embodiments, $R^1$ is hydrogen; and $R^2$ is tetrazolyl-$C_{10}$-alkyl, wherein the teterazolyl is unsubstituted. In certain embodiments, $R^1$ is hydrogen; and $R^2$ is $C_6$-alkyl substituted at $C_3$ with a tetrazolyl and $C_6$ with a tetrazolyl, wherein each teterazolyl is unsubstituted.

In certain embodiments, the compound of formula (I) is selected from the group consisting of: 1,4-di(1H-tetrazol-5-yl)butane ("BDTZ"); 5-phenyl-1H-tetrazole ("PhTZ"); 1,2,3,4-tetrazole ("T"); 1,6-di(1H-tetrazol-5-yl)hexane ("HDTZ"); 1,7-di(1H-tetrazol-5-yl)heptane ("HeDTZ"); 1,8-di(1H-tetrazol-5-yl)octane ("ODTZ"); and 5,5',5"-(hexane-1,3,6-triyl)tris(1H-tetrazole) ("TCH-TZ").

In certain embodiments, the compound of formula (I) is selected from the group consisting of: 1,6-di(1H-tetrazol-5-yl)hexane ("HDTZ"); 1,7-di(1H-tetrazol-5-yl)heptane ("HeDTZ"); 1,8-di(1H-tetrazol-5-yl)octane ("ODTZ"); and 5,5',5"-(hexane-1,3,6-triyl)tris(1H-tetrazole) ("TCH-TZ").

In another aspect, the tetrazole component is a compound of formula (II), or a salt thereof,

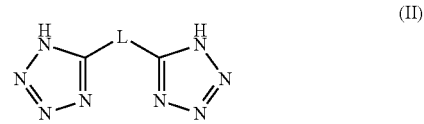

(II)

wherein,

L is selected from the group consisting of alkylenyl, alkenylenyl, and alkynylenyl, wherein said alkylenyl, alkenylenyl, and alkynylenyl are each independently substituted or unsubstituted with one or more suitable substituents.

In certain embodiments, L is $C_1$-$C_{32}$-alkylenyl, $C_2$-$C_{32}$-alkenylenyl, or $C_2$-$C_{32}$-alkynylenyl, wherein said alkylenyl, alkenylenyl, and alkynylenyl are each independently substituted or unsubstituted with one or more suitable substituents. In certain embodiments, L is $C_1$-$C_{24}$-alkylenyl, $C_2$-$C_{24}$-alkenylenyl, or $C_2$-$C_{24}$-alkynylenyl, wherein said alkylenyl, alkenylenyl, and alkynylenyl are each independently substituted or unsubstituted with one or more suitable substituents. In certain embodiments, L is $C_1$-$C_{10}$-alkylenyl, $C_2$-$C_{10}$-alkenylenyl, or $C_2$-$C_{10}$-alkynylenyl, wherein said alkylenyl, alkenylenyl, and alkynylenyl are each independently substituted or unsubstituted with one or more suitable substituents. In certain embodiments, L is $C_1$-$C_6$-alkylenyl, $C_2$-$C_6$-alkenylenyl, or $C_2$-$C_6$-alkynylenyl, wherein said alkylenyl, alkenylenyl, and alkynylenyl are each independently substituted or unsubstituted with one or more suitable substituents. In certain embodiments, L is $C_6$-$C_{10}$-alkylenyl, wherein said alkylenyl is independently substituted or unsubstituted with one or more suitable substituents.

In certain embodiments, L is $C_1$-$C_{32}$-alkylenyl, $C_2$-$C_{32}$-alkenylenyl, or $C_2$-$C_{32}$-alkynylenyl, wherein said alkylenyl, alkenylenyl, and alkynylenyl are each independently substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is $C_1$-$C_{24}$-alkylenyl, $C_2$-$C_{24}$-alkenylenyl, or $C_2$-$C_{24}$-alkynylenyl, wherein said alkylenyl, alkenylenyl, and alkynylenyl are each independently substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is $C_1$-$C_{10}$-alkylenyl, $C_2$-$C_{10}$-alkenylenyl, or $C_2$-$C_{10}$-alkynylenyl, wherein said alkylenyl, alkenylenyl, and alkynylenyl are each independently substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is $C_1$-$C_6$-alkylenyl, $C_2$-$C_6$-alkenylenyl, or $C_2$-$C_6$-alkynylenyl, wherein said alkylenyl, alkenylenyl, and alkynylenyl are each independently substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is $C_6$-$C_{10}$-alkylenyl, wherein said alkylenyl is independently substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl.

In certain embodiments, L is unsubstituted $C_1$-$C_{10}$-alkylenyl. In certain embodiments, L is unsubstituted $C_1$-$C_6$-alkylenyl. In certain embodiments, L is unsubstituted $C_6$-$C_{10}$-alkylenyl. In certain embodiments, L is $C_1$-$C_{10}$-alkylenyl substituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is $C_1$-$C_6$-alkylenyl, substituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is $C_6$-$C_{10}$-alkylenyl, substituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl.

In certain embodiments, L is $C_4$-alkylenyl, wherein said alkylenyl is substituted or unsubstituted with one or more suitable substituents. In certain embodiments, L is $C_4$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_4$-alkylenyl.

In certain embodiments, L is $C_5$-alkylenyl, wherein said alkylenyl is substituted or unsubstituted with one or more suitable substituents. In certain embodiments, L is $C_5$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_5$-alkylenyl.

In certain embodiments, L is $C_6$-alkylenyl, wherein said alkylenyl is substituted or unsubstituted with one or more suitable substituents. In certain embodiments, L is $C_6$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_6$-alkylenyl.

In certain embodiments, L is $C_7$-alkylenyl, wherein said alkylenyl is substituted or unsubstituted with one or more suitable substituents. In certain embodiments, L is $C_7$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_7$-alkylenyl.

In certain embodiments, L is $C_8$-alkylenyl, wherein said alkylenyl is substituted or unsubstituted with one or more suitable substituents. In certain embodiments, L is $C_8$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_8$-alkylenyl.

In certain embodiments, L is $C_9$-alkylenyl, wherein said alkylenyl is substituted or unsubstituted with one or more suitable substituents. In certain embodiments, L is $C_9$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_9$-alkylenyl.

In certain embodiments, L is $C_{10}$-alkylenyl, wherein said alkylenyl is substituted or unsubstituted with one or more suitable substituents. In certain embodiments, L is $C_{10}$-alkylenyl, wherein said alkylenyl is substituted or unsubstituted with 1 to 3 substituents independently selected from the group consisting of —F, —Cl, —NO$_2$, —CN, —OH, —NH$_2$, $C_1$-$C_6$ alkyl, $C_1$-$C_6$ haloalkyl, $C_1$-$C_6$ alkoxy, —CO$_2$R$^3$, and —CON(R$^4$)$_2$, wherein R$^3$ and R$^4$, at each occurrence, are each independently selected from the group consisting of hydrogen and $C_1$-$C_6$ alkyl. In certain embodiments, L is unsubstituted $C_{10}$-alkylenyl.

In certain embodiments, L is $C_1$-$C_{10}$-alkylenyl or $C_6$-$C_{10}$-alkylenyl, substituted with one, two, or three heteraryl groups, wherein said heteroaryl groups are substituted or unsubstituted. In certain embodiments, L is $C_1$-$C_{10}$-alkylenyl or $C_6$-$C_{10}$-alkylenyl, substituted with one, two, or three tetrazolyl groups, wherein said tetrazolyl groups are substituted or unsubstituted. In certain embodiments, L is $C_1$-$C_{10}$-alkylenyl or $C_6$-$C_{10}$-alkylenyl, substituted with one, two, or three tetrazolyl groups, wherein said tetrazolyl groups are unsubstituted.

In certain embodiments, the compound of formula (II) is selected from the group consisting of: 1,6-di(1H-tetrazol-5-yl)hexane ("HDTZ"); 1,7-di(1H-tetrazol-5-yl)heptane ("HeDTZ"); 1,8-di(1H-tetrazol-5-yl)octane ("ODTZ"); and 5,5',5''-(hexane-1,3,6-triyl)tris(1H-tetrazole) ("TCH-TZ").

The tetrazole component may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

The tetrazole component may constitute from about 0.01 wt % to about 100 wt % of the corrosion inhibitor composition, from about 0.1 wt % to about 100 wt % the corrosion inhibitor composition, from about 0.5 wt % to about 10 wt % of the corrosion inhibitor composition, or from about 1 wt % to about 3 wt % of the corrosion inhibitor composition, based on total weight of the composition. A composition of the invention may comprise from 0.01 wt % to 100 wt % tetrazole component, from 0.1 wt % to 100 wt % tetrazole component, from 0.5 wt % to 10 wt % tetrazole component, 0.5 wt % to 3 wt % tetrazole component, 0.5 wt % to 2 wt % tetrazole component, or from 1 wt % to 3 wt % tetrazole component, based on total weight of the composition. A composition of the invention may comprise about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, about 30 wt %, about 31 wt %, about 32 wt %, about 33 wt %, about 34 wt %, about 35 wt %, about 36 wt %, about 37 wt %, about 38 wt %, about 39 wt %, about 40 wt %, about 41 wt %, about 42 wt %, about 43 wt %, about 44 wt %, about 45 wt %, about 46 wt %, about 47 wt %, about 48 wt %, about 49 wt %, or about 50 wt % tetrazole component, based on total weight of the composition. A composition of the invention may comprise 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, 2.1 wt %, 2.2 wt %, 2.3 wt %, 2.4 wt %, 2.5 wt %, 2.6 wt %, 2.7 wt %, 2.8 wt %, 2.9 wt %, 3.0 wt %, 3.1 wt %, 3.2 wt %, 3.3 wt %, 3.4 wt %, 3.5 wt %, 3.6 wt %, 3.7 wt %, 3.8 wt %, 3.9 wt %, 4.0 wt %, 4.1 wt %, 4.2 wt %, 4.3 wt %, 4.4 wt %, 4.5 wt %, 4.6 wt %, 4.7 wt %, 4.8 wt %, 4.9 wt %, or 5.0 wt % tetrazole component, based on total weight of the composition. Each system may have its own requirements, and the weight percent of tetrazole(s) in the composition may vary with the system in which it is used.

The compositions of the invention may provide a dose of the tetrazole component ranging from about 0.01 to about 5,000 ppm. In certain embodiments, the compositions may provide a tetrazole concentration of about 1 parts per million (ppm) to about 1,000,000 ppm, about 1 parts per million (ppm) to about 100,000 ppm, or about 10 ppm to about 75,000 ppm. The compositions may provide a tetrazole concentration of about 100 ppm to about 10,000 ppm, about 200 ppm to about 8,000 ppm, or about 500 ppm to about 6,000 ppm. In certain embodiments, the compositions may provide a tetrazole concentration of 0.1 ppm, 0.5 ppm, 1 ppm, 2 ppm, 3 ppm, 4 ppm, 5 ppm, 6 ppm, 7 ppm, 8 ppm, 9 ppm, 10 ppm, 20 ppm, 100 ppm, 200 ppm, 500 ppm, 1,000 ppm, 5,000 ppm, 10,000 ppm, 20,000 ppm, or greater. In certain embodiments, the compositions provide a tetrazole concentration of 0.125 ppm, 0.25 ppm, 0.625 ppm, 1 ppm, 1.25 ppm, 2.5 ppm, 5 ppm, 10 ppm, or 20 ppm. Each system may have its own dose level requirements, and the effective dose level of a composition to sufficiently reduce the rate of corrosion may vary with the system in which it is used.

b. Tracer

The compositions disclosed herein may include a tracer. The tracer may be a fluorescent tracer. These fluorescent tracers may or may not be appreciably or significantly affected by any other chemistry in a cooling water process, or by the other system parameters such as pH, temperature, ionic strength, redox potential, microbiological activity or biocide concentration.

Representative fluorescent tracers include, but are not limited to, 3,6-acridinediamine, N,N,N',N'-tetramethyl-, monohydrochloride, also known as Acridine Orange (CAS Registry No. 65-61-2), 2-anthracenesulfonic acid sodium salt (CAS Registry No. 16106-40-4), 1,5-anthracenedisulfonic acid (CAS Registry No. 61736-91-2) and salts thereof, 2,6-anthracenedisulfonic acid (CAS Registry No. 61736-95-6) and salts thereof, 1,8-anthracenedisulfonic acid (CAS Registry No. 61736-92-3) and salts thereof, anthra[9,1,2-cde]benzo[rst]pentaphene-5,10-diol, 16,17-dimethoxy-, bis(hydrogen sulfate), disodium salt, also known as Anthrasol Green IBA (CAS Registry No. 2538-84-3, aka Solubilized Vat Dye), bathophenanthrolinedisulfonic acid disodium salt (CAS Registry No. 52746-49-3), amino 2,5-benzene disulfonic acid (CAS Registry No. 41184-20-7), 2-(4-aminophenyl)-6-methylbenzothiazole (CAS Registry No. 92-36-4), 1H-benz[de]isoquinoline-5-sulfonic acid, 6-amino-2,3-dihydro-2-(4-methylphenyl)-1,3-dioxo-, monosodium salt, also known as Brilliant Acid Yellow 8G (CAS Registry No. 2391-30-2, aka Lissamine Yellow FF, Acid Yellow 7), phenoxazin-5-ium, 1-(aminocarbonyl)-7-(diethylamino)-3,4-dihydroxy-, chloride, also known as Celestine Blue (CAS Registry No. 1562-90-9), benzo[a]phenoxazin-7-ium, 5,9-diamino-, acetate, also known as cresyl violet acetate (CAS Registry No. 10510-54-0), 4-dibenzofuransulfonic acid (CAS Registry No. 42137-76-8), 3-dibenzofuransulfonic acid (CAS Registry No. 215189-98-3), 1-ethylquinaldinium iodide (CAS Registry No. 606-53-3), fluorescein (CAS Registry No. 2321-07-5), fluorescein, sodium salt (CAS Registry No. 518-47-8, aka Acid Yellow 73, Uranine), Keyfluor White ST (CAS Registry No. 144470-48-4, aka Flu. Bright 28), benzenesulfonic acid, 2,2'-(1,2-ethenediyl)bis[5-[[4-[bis(2-hydroxyethyl)amino]-6-[(4-sulfophen-yl)amino]-1,3,5-triazin-2-yl]amino]-, tetrasodium salt, also known as Keyfluor White CN (CAS Registry No. 16470-24-9), C.I. Fluorescent Brightener 230, also known as Leucophor BSB (CAS Registry No. 68444-86-0), benzenesulfonic acid, 2,2'-(1,2-ethenediyl)bis[5-[[4-bis(2-hydroxyethyl)amino]-6-[(4-sulfophen-yl)amino]-1,3,5-triazin-2-yl]amino]-, tetrasodium salt, also known as Leucophor BMB (CAS Registry No. 16470-24-9, aka Leucophor U, Flu. Bright. 290), 9,9'-biacridinium, 10,10'-dimethyl-, dinitrate, also known as Lucigenin (CAS Registry No. 2315-97-1, aka bis-N-methylacridinium nitrate), 1-deoxy-1-(3,4-dihydro-7,8-dimethyl-2,4-dioxobenzo[g]pteridin-1-0(2H)-yl)-D-ribitol, also known as Riboflavin or Vitamin B2 (CAS Registry No. 83-88-5), mono-, di-, or tri-sulfonated napthalenes, including but not limited to 1,5-naphthalenedisulfonic acid, disodium salt (hydrate) (CAS Registry No. 1655-29-4, aka 1,5-NDSA hydrate), 2-amino-1-naphthalenesulfonic acid (CAS Registry No. 81-16-3), 5-amino-2-naphthalenesulfonic acid (CAS Registry No. 119-79-9), 4-amino-3-hydroxy-1-naphthalenesulfonic acid (CAS Registry No. 90-51-7), 6-amino-4-hydroxy-2-naphthalenesulfonic acid (CAS Registry No. 116-63-2), 7-amino-1,3-naphthalenesulfonic acid, potassium salt (CAS Registry No. 79873-35-1), 4-amino-5-hydroxy-2,7-naphthalenedisulfonic acid (CAS Registry No. 90-20-0), 5-dimethylamino-1-naphthalenesulfonic acid (CAS Registry No. 4272-77-9), 1-amino-4-naphthalene sulfonic acid (CAS Registry No. 84-86-6), 1-amino-7-naphthalene sulfonic acid (CAS Registry No. 119-28-8), 2,6-naphthalenedicarboxylic acid, dipotassium salt (CAS Registry No. 2666-06-0), 3,4,9,10-perylenetetracarboxylic acid (CAS Registry No. 81-32-3), C.I. Fluorescent Brightener 191, also known as Phorwite CL (CAS Registry No. 12270-53-0), C.I. Fluorescent Brightener 200, also known as Phorwite BKL (CAS Registry No. 61968-72-7), benzenesulfonic acid, 2,2'-(1,2-ethenediyl)bis[5-(4-phenyl-2H-1,2,3-triazol-2-yl)-, dipotassium salt, also known as Phorwite BHC 766 (CAS Registry No. 52237-03-3), benzenesulfonic acid, 5-(2H-naphtho[1,2-d]triazol-2-yl)-2-(2-phenylethenyl)-, sodium salt, also known as Pylaklor White S-15A (CAS Registry No. 6416-68-8), 1,3,6,8-pyrenetetrasulfonic acid, tetrasodium salt (CAS Registry No. 59572-10-0), pyranine, (CAS Registry No. 6358-69-6, aka 8-hydroxy-1,3,6-pyrenetrisulfonic acid, trisodium salt), quinoline (CAS Registry No. 91-22-5), 3H-phenoxazin-3-one, 7-hydroxy-, 10-oxide, also known as Rhodalux (CAS Registry No. 550-82-3), xanthylium, 9-(2,4-dicarboxyphenyl)-3,6-bis(diethylamino)-, chloride, disodium salt, also known as Rhodamine WT (CAS Registry No. 37299-86-8), phenazinium, 3,7-diamino-2,8-dimethyl-5-phenyl-, chloride, also known as Safranine O (CAS Registry No. 477-73-6), C.I. Fluorescent Brightener 235, also known as Sandoz CW (CAS Registry No. 56509-06-9), benzenesulfonic acid, 2,2'-(1,2-ethenediyl)bis[5-[[4-[bis(2-hydroxyethyl)amino]-6-[(4-sulfophen-yl)amino]-1,3,5-triazin-2-yl]amino]-, tetrasodium salt, also known as Sandoz CD (CAS Registry No. 16470-24-9, aka Flu. Bright. 220), benzenesulfonic acid, 2,2'-(1,2-ethenediyl)bis[5-[[4-[(2-hydroxypropyl)amino]-6-(phenylamino)-1-,3,5-triazin-2-yl]amino]-, disodium salt, also known as Sandoz TH-40 (CAS Registry No. 32694-95-4), xanthylium, 3,6-bis(diethylamino)-9-(2,4-disulfophenyl)-, inner salt, sodium salt, also known as Sulforhodamine B (CAS Registry No. 3520-42-1, aka Acid Red 52), benzenesulfonic acid, 2,2'-(1,2-ethenediyl)bis[5-[[4-[(aminomethyl)(2-hydroxyethyl)amino]-6-(ph-enylamino)-1,3,5-triazin-2-yl]amino]-, disodium salt, also known as Tinopal 5BM-GX (CAS Registry No. 169762-28-1), Tinopol DCS (CAS Registry No. 205265-33-4), benzenesulfonic acid, 2,2'-([1,1'-biphenyl]-4,4'-diyldi-2,1-ethenediyl)bis-, disodium salt also known as Tinopal CBS-X (CAS Registry No. 27344-41-8), benzenesulfonic acid, 5-(2H-naphtho[1,2-d]triazol-2-yl)-2-(2-phenylethenyl)-, sodium salt, also known as Tinopal RBS 200, (CAS Registry No. 6416-68-8), 7-benzothiazolesulfonic acid, 2,2'-(1-triazene-1,3-diyldi-4,1-phenylene)bis[6-methyl-, disodium salt, also known as Titan Yellow (CAS Registry No. 1829-00-1, aka Thiazole Yellow G), and all ammonium, potassium and sodium salts thereof, and all like agents and suitable mixtures thereof.

Preferred tracers include 1-deoxy-1-(3,4-dihydro-7,8-dimethyl-2,4-dioxobenzo[g]pteridin-10(2H)-yl)-D-ribitol, also known as Riboflavin or Vitamin B2 (CAS Registry No. 83-88-5), fluorescein (CAS Registry No. 2321-07-5), fluorescein, sodium salt (CAS Registry No. 518-47-8, aka Acid Yellow 73, Uranine), 2-anthracenesulfonic acid sodium salt (CAS Registry No. 16106-40-4), 1,5-anthracenedisulfonic acid (CAS Registry No. 61736-91-.sup.2) and salts thereof, 2,6-anthracenedisulfonic acid (CAS Registry No. 61736-95-6) and salts thereof, 1,8-anthracenedisulfonic acid (CAS Registry No. 61736-92-3) and salts thereof, mono-, di-, or tri-sulfonated napthalenes, including but not limited to 1,5-naphthalenedisulfonic acid, disodium salt (hydrate) (CAS Registry No. 1655-29-4, aka 1,5-NDSA hydrate), 2-amino-1-naphthalenesulfonic acid (CAS Registry No. 81-16-3), 5-amino-2-naphthalenesulfonic acid (CAS Registry No. 119-79-9), 4-amino-3-hydroxy-1-naphthalenesulfonic acid (CAS Registry No. 90-51-7), 6-amino-4-hydroxy-2-naphthalenesulfonic acid (CAS Registry No. 116-63-2), 7-amino-1,3-naphthalenesulfonic acid, potassium salt (CAS Registry No. 79873-35-1), 4-amino-5-hydroxy-2,7-naphthalenedisulfonic acid (CAS Registry No. 90-20-0), 5-dimethylamino-1-naphthalenesulfonic acid (CAS Registry No. 4272-77-9), 1-amino-4-naphthalene sulfonic acid (CAS Registry No. 84-86-6), 1-amino-7-naphthalene sulfonic acid (CAS Registry No. 119-28-8), 2,6-naphthalenedicarboxylic acid, dipotassium salt (CAS Registry No. 2666-06-0), 3,4,9,10-perylenetetracarboxylic acid (CAS Registry No. 81-32-3), C.I. Fluorescent Brightener 191, also known as, Phorwite CL (CAS Registry No. 12270-53-0), C.I. Fluorescent Brightener 200, also known as Phorwite BKL (CAS Registry No. 61968-72-7), benzenesulfonic acid, 2,2'-(1,2-ethenediyl)bis [5-(4-phenyl-2H-1,2,3-triazol-2-yl)-dipotassium salt, also known as Phorwite BHC 766 (CAS Registry No. 52237-03-3), benzenesulfonic acid, 5-(2H-naphtho[1,2-d]triazol-2-yl)-2-(2-phenylethenyl)-, sodium salt, also known as Pylaklor White S-15A (CAS Registry No. 6416-68-8), pyranine, (CAS Registry No. 6358-69-6, aka 8-hydroxy-1,3,6-pyrenetrisulfonic acid, trisodium salt), quinoline (CAS Registry No. 91-22-5), 3H-phenoxazin-3-one, 7-hydroxy-, 10-oxide, also known as Rhodalux (CAS Registry No. 550-82-3), xanthylium, 9-(2,4-dicarboxyphenyl)-3,6-bis(diethylamino)-, chloride, disodium salt, also known as Rhodamine WT (CAS Registry No. 37299-86-8), phenazinium, 3,7-diamino-2,8-dimethyl-5-phenyl-, chloride, also known as Safranine O (CAS Registry No. 477-73-6), C.I. Fluorescent Brightener 235, also known as Sandoz CW (CAS Registry No. 56509-06-9), benzenesulfonic acid, 2,2'-(1,2-ethenediyl)bis[5-[[4-[bis(2-hydroxyethyl)amino]-6-[(4-sulfophen-yl)amino]-1,3,5-triazin-2-yl]amino]-, tetrasodium salt, also known as Sandoz CD (CAS Registry No. 16470-24-9, aka Flu. Bright. 220), benzenesulfonic acid, 2,2'-(1,2-ethenediyl)bis[5-[[4-[(2-hydroxypropyl)amino]-6-(phenylamino)-1-,3,5-triazin-2-yl]amino]-, disodium salt, also known as Sandoz TH-40 (CAS Registry No. 32694-95-4), xanthylium, 3,6-bis(diethylamino)-9-(2,4-disulfophenyl)-, inner salt, sodium salt, also known as Sulforhodamine B (CAS Registry No. 3520-42-1, aka Acid Red 52), benzenesulfonic acid, 2,2'-(1,2-ethenediyl)bis[5-[[4-Raminomethyl)(2-hydroxyethyl)amino]-6-(ph-enylamino)-1,3,5-triazin-2-yl]amino]-, disodium salt, also known as Tinopal 5BM-GX (CAS Registry No. 169762-28-1), Tinopol DCS (CAS Registry No. 205265-33-4), benzenesulfonic acid, 2,2'-([1,1'-biphenyl]-4,4'-diyldi-2,1-ethenediyl)bis-, disodium salt, also known as Tinopal CBS-X (CAS Registry No. 27344-41-8), benzenesulfonic acid, 5-(2H-naphtho[1,2-d]triazol-2-yl)-2-(2-phenylethenyl)-, sodium salt, also known as Tinopal RBS 200, (CAS Registry No. 6416-68-8), 7-benzothiazolesulfonic acid, 2,2'-(1-triazene-1,3-diyldi-4,1-phenylene)bis[6-methyl-, disodium salt, also known as Titan Yellow (CAS Registry No. 1829-00-1, aka Thiazole Yellow G), and all ammonium, potassium and sodium salts thereof, and all like agents and suitable mixtures thereof.

More preferred fluorescent tracers include fluorescein, sodium salt (CAS Registry No. 518-47-8, aka Acid Yellow 73, Uranine); 1,5-naphthalenedisulfonic acid disodium salt (hydrate) (CAS Registry No. 1655-29-4, aka 1,5-NDSA hydrate); xanthylium, 9-(2,4-dicarboxyphenyl)-3,6-bis(diethylamino)-, chloride, disodium salt, also known as Rhodamine WT (CAS Registry No. 37299-86-8); 1-deoxy-1-(3, 4-dihydro-7,8-dimethyl-2,4-dioxobenzo[g]pteridin-10(2H)-yl)-D-ribitol, also known as Riboflavin or Vitamin B2 (CAS Registry No. 83-88-5); fluorescein (CAS Registry No. 2321-07-5); 2-anthracenesulfonic acid sodium salt (CAS Registry No. 16106-40-4); 1,5-anthracenedisulfonic acid (CAS Registry No. 61736-91-2) and salts thereof; 2,6-anthracenedisulfonic acid (CAS Registry No. 61736-95-6) and salts thereof; 1,8-anthracenedisulfonic acid (CAS Registry No. 61736-92-3) and salts thereof; and mixtures thereof. The fluorescent tracers listed above are commercially available from a variety of different chemical supply companies.

In addition to the tracers listed above, those skilled in the art will recognize that salts using alternate counter ions may also be used. Thus, for example, anionic tracers, which have $Na^+$ as a counter ion, could also be used in forms where the counter ion is chosen from $K^+$, $NH_4^+$, $Ca^{+2}$, $Mg^{-2}$ or other appropriate counter ions. Similarly, cationic tracers may have a variety of counter ions, for example: $Cl^-$, $SO_4^{-2}$, $PO_4^{-3}$, $HPO_4^{-2}$; $H_2PO_4^-$; $CO_3^{-2}$; $HCO_3^-$; or other appropriate counter ions.

In certain embodiments, the tetrazole component is tagged with a fluorescent moiety.

The dosage of the fluorescent tracer may be an amount that is at least sufficient to provide a measurable concentration in the treated fluid. Typical doses range from about 50 ppt (parts per trillion) to about 100 ppb (parts per billion), preferably from about 0.1 ppb to about 10 ppb, based on fluorescent agent concentration. Note that 50 ppt is about the detection limit of currently available industrial fluorometers. Improvements in fluorometer technology are likely to reduce this detection limit and are envisioned.

The tracer may constitute from about 0.001 wt % to about 10 wt % of the corrosion inhibitor composition, from about 0.01 wt % to about 5 wt % the corrosion inhibitor composition, from about 0.1 wt % to about 3 wt % of the corrosion inhibitor composition, or from about 0.5 wt % to about 1.5 wt % of the corrosion inhibitor composition, based on total weight of the composition. A composition of the invention may comprise from 0.001 wt % to 10 wt % tracer, from 0.01 wt % to 5 wt % tracer, from 0.1 wt % to 3 wt % tracer, or from 0.5 wt % to 1.5 wt % tracer, based on total weight of the composition. A composition of the invention may comprise about 0.001 wt %, about 0.01 wt %, about 0.05 wt %, about 0.1 wt %, about 0.5 wt %, about 1 wt %, about 2 wt %, or about 3 wt % tracer, based on total weight of the composition. A composition of the invention may comprise 1 wt % tracer, based on total weight of the composition. Each system may have its own requirements, and the weight percent of tracer(s) in the composition may vary with the system in which it is used.

The fluorescent tracers can be detected by utilizing a variety of different and suitable techniques. For example, fluorescence emission spectroscopy on a substantially continuous basis, at least over a given time period, is one of the preferred analytical techniques according to an embodiment of this invention. One method for the continuous on-stream measuring of chemical tracers by fluorescence emission spectroscopy and other analysis methods is described in U.S. Pat. No. 4,992,380, incorporated herein by reference.

Examples of fluorometers that may be used in the practice of this invention include the Xe II and TRASAR® 8000 fluorometer (available from Nalco Company, Naperville, Ill.); the Hitachi F-4500 fluorometer (available from Hitachi through Hitachi Instruments Inc., San Jose, Calif.); the JOBIN YVON FluoroMax-3 "SPEX" fluorometer (available from JOBIN YVON Inc., Edison, N.J.); and the Gilford Fluoro-IV spectrophotometer or the SFM 25 (available from Bio-tech Kontron through Research Instruments International, San Diego, Calif.). It should be appreciated that the foregoing list is not comprehensive and is intended only to show examples of representative fluorometers. Other commercially available fluorometers and modifications thereof can also be used in this invention.

It should be appreciated that a variety of other suitable analytical techniques may be utilized to measure the amount of fluorescent tracers. Examples of such techniques include combined HPLC-fluorescence analysis, colorimetry analysis, ion selective electrode analysis, transition metal analysis, chemiluminescence, pulsed fluorescence measurements, and the like.

In an embodiment, the present invention includes a controller programmed with an algorithm and which continuously (i.e. within the timescale of the retention time, typically every few minutes) makes incremental changes in the treating agent dosage and performs the calculations described above so as to maintain the treating agent residuals at the desired set point. The controller can be configured and/or adjusted in a variety of different and suitable ways. Alternative methods could include using three or more points to measure the fluorescence response and then use analytical curve fitting methods to determine optimal dosage. The controller can be either hard wired (e.g., electrical communication cable), or can communicate with the other components described herein by wireless communication (e.g., wireless RF interface), a pneumatic interface and the like.

c. Scale Inhibitors

The compositions disclosed herein may include a scale inhibitor. Suitable scale inhibitors include, but are not limited to, phosphates, phosphate esters, phosphoric acids, phosphonates, phosphonic acids, polyacrylamides, salts of acrylamido-methyl propane sulfonate/acrylic acid copolymer (AMPS/AA), phosphinated maleic copolymer (PHOS/MA), and salts of a polymaleic acid/acrylic acid/acrylamido-methyl propane sulfonate terpolymer (PMA/AMP S).

Scale inhibitors include 1-hydroxyethylidene-1,1-diphosphonic acid (abbreviated "HEDP"), 2-Phosphonobutane-1, 2,4-tricarboxylic acid (abbreviated "PBTC"), aminotri(methylenephosphonic acid (abbreviated "AMP"), hexamethylene diamine tetra(methylene phosphonic acid (abbreviated "HMDTMP") and polyamino polyether methylenephosphonic acid (abbreviated "PAPEMP"), organic polymers such as polyacrylic acid, polyacrylates, polymaleic acid, maleic anhydride/ethyl acrylate/vinyl acrylate terpolymer and alkyl epoxy carboxylate (abbreviated "AEC"), phosphinocarboxylic acids, such as phosphinosuccinate oligomers (abbreviated as "PSO"), and phosphonocarboxylic acids, such as phosphonocarboxylic (sulfonated) copolymer (abbreviated "POCA", sold as Belclene 494).

The scale inhibitor may constitute from about 1 wt % to about 80 wt % of the corrosion inhibitor composition, from about 1 wt % to about 50 wt % the corrosion inhibitor composition, from about 2 wt % to about 20 wt % the corrosion inhibitor composition, or from about 5 wt % to about 15 wt % of the corrosion inhibitor composition, based on total weight of the composition. A composition of the invention may comprise from 1 wt % to 30 wt % scale inhibitor, from 2 wt % to 20 wt % scale inhibitor, from 5 wt % to 20 wt % scale inhibitor, from 5 wt % to 15 wt % scale inhibitor, or from 10 wt % to 20 wt % scale inhibitor, based on total weight of the composition. A composition of the invention may comprise about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, about 10.5 wt %, about 11.0 wt %, about 11.5 wt %, about 12.0 wt %, about 12.5 wt %, about 13.0 wt %, about 13.5 wt %, about 14.0 wt %, about 14.5 wt %, about 15.0 wt %, about 15.5 wt %, about 16.0 wt %, about 16.5 wt %, or about 17.0 wt % scale inhibitor, based on total weight of the composition. Each system may have its own requirements, and the weight percent of scale inhibitor(s) in the composition may vary with the system in which it is used.

d. Dispersants

The compositions disclosed herein may include a dispersant. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate) and the triamine- and tetramine-polymethylene phosphonates with 2-4 methylene groups between each N atom, at least 2 of the numbers of methylene groups in each phosphonate being different. Other suitable dispersion agents include lignin or derivatives of lignin such as lignosulfonate and naphthalene sulfonic acid and derivatives.

The dispersant may constitute from about 1 wt % to about 80 wt % of the corrosion inhibitor composition, from about 1 wt % to about 30 wt % the corrosion inhibitor composition, from about 2 wt % to about 25 wt % the corrosion inhibitor composition, or from about 5 wt % to about 20 wt % of the corrosion inhibitor composition, based on total weight of the composition. A composition of the invention may comprise from 1 wt % to 30 wt % dispersant, from 2 wt % to 25 wt % dispersant, from 5 wt % to 25 wt % dispersant, or from 5 wt % to 20 wt % dispersant, based on total weight of the composition. A composition of the invention may comprise about 10.0 wt %, about 10.5 wt %, about 11.0 wt %, about 11.5 wt %, about 12.0 wt %, about 12.5 wt %, about 13.0 wt %, about 13.5 wt %, about 14.0 wt %, about 14.5 wt %, about 15.0 wt %, about 15.5 wt %, about 16.0 wt %, about 16.5 wt %, about 17.0 wt %, about 17.5 wt %, about 18.0 wt %, about 18.5 wt %, about 19.0 wt %, about 19.5 wt %, about 20.0 wt %, about 20.5 wt %, about 21.0 wt %, about 21.5 wt %, about 22.0 wt %, about 22.5 wt %, about 23.0 wt %, about 23.5 wt %, about 24.0 wt %, about 24.5 wt %, or about 25.0 wt % dispersant, based on total weight of the composition. Each system may have its own requirements, and the weight percent of dispersant(s) in the composition may vary with the system in which it is used.

e. Acid

The compositions disclosed herein may include an acid. The acid may be selected from the group consisting of mineral acids, organic acids, and a combination thereof. The mineral acids may be selected from the group consisting of hydrochloric acid, sulfuric acid, amido sulfuric acid (98%), nitric acid, phosphoric acid, hydrofluoric acid, sulfamic acid, and combinations thereof; and said organic acids may be selected from the group consisting of citric acid and its salts, formic acid, acetic acid, peracids including peracetic acid, peroxyacetic acid and peroxyformic acid, glycolic acid (hydroxyacetic acid), oxalic acid, propionic acid, lactic acid (hydroxypropionic acid), butyric acid, and combinations thereof. These acids are commercial chemicals available from a chemical supply company. These acids can be purchased in dry or in liquid form or in formulations that contain other functional chemicals which also can be in dry or liquid form.

The acid may constitute from about 1 wt % to about 10 wt % of the corrosion inhibitor composition, from about 2 wt % to about 8 wt % the corrosion inhibitor composition, or from about 4 wt % to about 6 wt % of the corrosion inhibitor composition, based on total weight of the composition. A composition of the invention may comprise from 1 wt % to 10 wt % acid, from 2 wt % to 8 wt % acid, from 3 wt % to 7 wt % acid, or from 4 wt % to 6 wt % acid, based on total weight of the composition. A composition of the invention may comprise about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, or about 10.0 wt % acid, based on total weight of the composition. Each system may have its own requirements, and the weight percent of acid(s) in the composition may vary with the system in which it is used.

f. Base

The compositions disclosed herein may include a base. The base may be selected from the group consisting of alkali hydroxides, alkali carbonates, alkali bicarbonates, alkaline earth metal hydroxides, alkaline earth metal carbonates, alkaline earth metal bicarbonates and mixtures or combinations thereof. Exemplary bases include NaOH, KOH, $Ca(OH)_2$, CaO, $Na_2CO_3$, $KHCO_3$, $K_2CO_3$, $NaHCO_3$, MgO, and $Mg(OH)_2$.

The base may constitute from about 1 wt % to about 40 wt % of the corrosion inhibitor composition, from about 5 wt % to about 30 wt % the corrosion inhibitor composition, or from about 10 wt % to about 25 wt % of the corrosion inhibitor composition, based on total weight of the composition. A composition of the invention may comprise from 1 wt % to 40 wt % base, from 5 wt % to 30 wt % base, from 5 wt % to 25 wt % base, or from 10 wt % to 25 wt % base, based on total weight of the composition. A composition of the invention may comprise about 1.0 wt %, about 1.5 wt %, about 2.0 wt %, about 2.5 wt %, about 3.0 wt %, about 3.5 wt %, about 4.0 wt %, about 4.5 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 9.5 wt %, about 10.0 wt %, about 10.5 wt %, about 11.0 wt %, about 11.5 wt %, about 12.0 wt %, about 12.5 wt %, about 13.0 wt %, about 13.5 wt %, about 14.0 wt %, about 14.5 wt %, about 15.0 wt %, about 15.5 wt %, about 16.0 wt %, about 16.5 wt %, about 17.0 wt %, about 17.5 wt %, about 18.0 wt %, about 18.5 wt %, about 19.0 wt %, about 19.5 wt %, about 20.0 wt %, about 20.5 wt %, about 21.0 wt %, about 21.5 wt %, about 22.0 wt %, about 22.5 wt %, about 23.0 wt %, about 23.5 wt %, about 24.0 wt %, about 24.5 wt %, or about 25.0 wt % base, based on total weight of the composition. Each system may have its own requirements, and the weight percent of base(s) in the composition may vary with the system in which it is used.

g. Solvents

The compositions disclosed herein may include a solvent. Suitable solvents include, but are not limited to, alcohols, hydrocarbons, ketones, ethers, aromatics, amides, nitriles, sulfoxides, esters, glycol ethers, aqueous systems, and combinations thereof. In certain embodiments, the solvent is water, isopropanol, methanol, ethanol, 2-ethylhexanol, heavy aromatic naphtha, toluene, ethylene glycol, ethylene glycol monobutyl ether (EGMBE), diethylene glycol monoethyl ether, or xylene. Representative polar solvents suitable for formulation with the composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like. Representative non-polar solvents suitable for formulation with the composition include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like.

In certain embodiments, the solvent is a polyhydroxylated solvent, a polyether, an alcohol, or a combination thereof. In certain embodiments, the solvent is monoethyleneglycol, methanol, dimethyl sulfoxide (DMSO), dimethylformamide (DMF), tetrahydrofuran (THF), or a combination thereof.

A composition of the invention may comprise from 0 to 99 percent, 1 to 98 percent, 20 to 50 percent, 25 to 45 percent, or 30 to 40 percent by weight of one or more solvents, based on total weight of the composition. In certain embodiments, a composition of the invention comprises about 20%, about 25%, about 30%, about 35%, about 40%, about 45%, about 50%, about 55%, about 60%, about 65%, about 70%, about 75%, about 80%, about 85%, about 90%, or about 95% by weight of one or more solvents, based on total weight of the composition. In certain embodiments, a composition of the invention comprises 30%, 31%, 32%, 33%, 34%, 35%, 36%, 37%, 38%, 39%, 40%, 41%, 42%, 43%, 44%, 45%, 46%, 47%, 48%, 49%, or 50% by weight of one or more solvents, based on total weight of the composition. In certain embodiments, a composition of the invention comprises 80%, 81%, 82%, 83%, 84%, 85%, 86%, 87%, 88%, 89%, 90%, 91%, 92%, 93%, 94%, 95%, 96%, 97%, 98%, or 99% by weight of one or more solvents, based on total weight of the composition.

h. Additional Corrosion Inhibitors

The compositions disclosed herein may include additional corrosion inhibitors. Suitable additional corrosion inhibitors for inclusion in the compositions include, but are not limited to, alkyl, hydroxyalkyl, alkylaryl, arylalkyl or arylamine quaternary salts; mono or polycyclic aromatic amine salts; imidazoline derivatives; mono-, di- or trialkyl or alkylaryl phosphate esters; phosphate esters of hydroxylamines; phosphate esters of polyols; and monomeric or oligomeric fatty acids.

Suitable alkyl, hydroxyalkyl, alkylaryl arylalkyl or arylamine quaternary salts include those alkylaryl, arylalkyl and arylamine quaternary salts of the formula $[N^-R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I. In certain embodiments, $R^{5a}$, $R^{6a}$, $R^{7a}$, and $R^{8a}$ are each independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I.

Suitable quaternary ammonium salts include, but are not limited to, tetramethyl ammonium chloride, tetraethyl ammonium chloride, tetrapropyl ammonium chloride, tetrabutyl ammonium chloride, tetrahexyl ammonium chloride, tetraoctyl ammonium chloride, benzyltrimethyl ammonium chloride, benzyltriethyl ammonium chloride, phenyltrimethyl ammonium chloride, phenyltriethyl ammonium chloride, cetyl benzyldimethyl ammonium chloride, hexadecyl trimethyl ammonium chloride, dimethyl alkyl benzyl quaternary ammonium compounds, monomethyl dialkyl benzyl quaternary ammonium compounds, trimethyl benzyl quaternary ammonium compounds, and trialkyl benzyl quaternary ammonium compounds, wherein the alkyl group can contain between about 6 and about 24 carbon atoms, about 10 and about 18 carbon atoms, or about 12 to about 16 carbon atoms. Suitable quaternary ammonium compounds (quats) include, but are not limited to, trialkyl, dialkyl, dialkoxy alkyl, monoalkoxy, benzyl, and imidazolinium quaternary ammonium compounds, salts thereof, the like, and combinations thereof. In certain embodiments, the quaternary ammonium salt is an alkylamine benzyl quaternary ammonium salt, a benzyl triethanolamine quaternary ammonium salt, or a benzyl dimethylaminoethanolamine quaternary ammonium salt.

In certain embodiments, the corrosion inhibitor may be a quaternary ammonium or alkyl pyridinium quaternary salt such as those represented by the general formula:

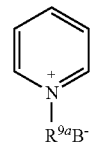

wherein $R^{9a}$ is an alkyl group, an aryl group, or an arylalkyl group, wherein said alkyl groups have from 1 to about 18 carbon atoms and B is Cl, Br or I. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium and an alkyl benzyl pyridinium chloride, preferably wherein the alkyl is a $C_1$-$C_6$ hydrocarbyl group. In certain embodiments, the corrosion inhibitor includes benzyl pyridinium chloride.

In certain embodiments, the corrosion inhibitor may be an imidazoline derived from a diamine, such as ethylene diamine (EDA), diethylene triamine (DETA), triethylene tetraamine (TETA) etc. and a long chain fatty acid such as tall oil fatty acid (TOFA). Suitable imidazolines include those of formula:

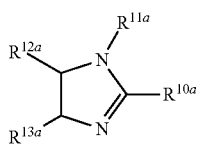

wherein $R^{12a}$ and $R^{13a}$ are independently a $C_1$-$C_6$ alkyl group or hydrogen, $R^{11a}$ is hydrogen, $C_1$-$C_6$ alkyl, $C_1$-$C_6$ hydroxyalkyl, or $C_1$-$C_6$ arylalkyl, and $R^{10a}$ is a $C_1$-$C_{20}$ alkyl or a $C_1$-$C_{20}$ alkoxyalkyl group. In a certain embodiments, $R^{11a}$, $R^{12a}$ and $R^{13a}$ are each hydrogen and $R^{10a}$ is the alkyl mixture typical in tall oil fatty acid (TOFA).

In certain embodiments, the corrosion inhibitor compound may be an imidazolinium compound of the following formula:

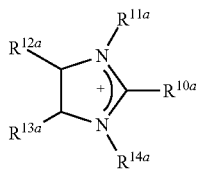

wherein $R^{12a}$ and $R^{13a}$ are independently a $C_1$-$C_6$ alkyl group or hydrogen, $R^{11a}$ and $R^{14a}$ are independently hydrogen, $C_1$-$C_6$ alkyl, $C_1$-$C_6$ hydroxyalkyl, or $C_1$-$C_6$ arylalkyl, and $R^{10}$ is a $C_1$-$C_{20}$ alkyl or a $C_1$-$C_{20}$ alkoxyalkyl group.

Suitable mono-, di- and trialkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethyl phosphate with triethylphosphate producing a more broad distribution of alkyl phosphate esters. Alternatively, the phosphate ester may be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor compound may further be a monomeric or oligomeric fatty acid. Preferred are $C_{14}$-$C_{22}$ saturated and unsaturated fatty acids as well as dimer, trimer and oligomer products obtained by polymerizing one or more of such fatty acids.

The corrosion inhibitor compound may be a triazole. The triazole may be selected from the group consisting of: benzotriazole, tolyltriazole, butylbenzotriazole, halo-benzotriazoles, halo-tolyltriazoles, nitrated-triazoles, and combinations thereof.

A composition of the invention may comprise from 0 to 80 percent, 0 to 60 percent, or 0 to 50 percent by weight of one or more additional corrosion inhibitors, based on total weight of the composition. In certain embodiments, a composition of the invention comprises from 0 to 10 percent by weight of one or more additional corrosion inhibitors, based on total weight of the composition. In certain embodiments, a composition of the invention comprises 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of one or more additional corrosion inhibitors, based on total weight of the composition. Each system may have its own requirements, and the weight percent of one or more additional corrosion inhibitors in the composition may vary with the system in which it is used.

i. Asphaltene Inhibitors

The compositions disclosed herein may include an asphaltene inhibitor. Suitable asphaltene inhibitors include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

j. Paraffin Inhibitors

The compositions disclosed herein may include a paraffin inhibitor. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable dispersants include, but are not limited to, dodecyl benzene sulfonate, oxyalkylated alkylphenols, and oxyalkylated alkylpnenolic resins.

k. Emulsifiers

The compositions disclosed herein may include an emulsifier. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

l. Water Clarifiers

The compositions disclosed herein may include a water clarifier. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

m. Emulsion Breakers

The compositions disclosed herein may include an emulsion breaker. Suitable emulsion breakers include, but are not limited to, dodecylbenzylsulfonic acid (DDBSA), the sodium salt of xylenesulfonic acid (NAXSA), epoxylated and propoxylated compounds, anionic cationic and nonionic surfactants, and resins, such as phenolic and epoxide resins.

n. Hydrogen Sulfide Scavengers

The compositions disclosed herein may include a hydrogen sulfide scavenger. Suitable additional hydrogen sulfide scavengers include, but are not limited to, oxidants (e.g., inorganic peroxides such as sodium peroxide, or chlorine dioxide), aldehydes (e.g., of 1-10 carbons such as formaldehyde or glutaraldehyde or (meth)acrolein), triazines (e.g., monoethanol amine triazine, monomethylamine triazine, and triazines from multiple amines or mixtures thereof), and glyoxal.

o. Gas Hydrate Inhibitors

The compositions disclosed herein may include a gas hydrate inhibitor. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, NaCl salt, KCl salt, $CaCl_2$ salt, $MgCl_2$ salt, $NaBr_2$ salt, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate). Suitable kinetic hydrate inhibitors and anti-agglomerates include, but are not limited to, polymers and copolymers, polysaccharides (such as hydroxy-ethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

p. Biocides

The compositions disclosed herein may include a biocide. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., bronopol and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

q. pH Modifiers

The compositions disclosed herein may include a pH modifier. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include NaOH, KOH, $Ca(OH)_2$, CaO, $Na_2CO_3$, $KHCO_3$, $K_2CO_3$, $NaHCO_3$, MgO, and $Mg(OH)_2$.

r. Surfactants

The compositions disclosed herein may include a surfactant. Suitable surfactants include, but are not limited to, anionic surfactants, cationic surfactants, zwitterionic surfactants, and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Cationic surfactants include alkyl trimethyl quaternary ammonium salts, alkyl dimethyl benzyl quaternary ammonium salts, dialkyl dimethyl quaternary ammonium salts, and imidazolinium salts. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopripionates and amphodipropionates, and alkyliminodiprionate.

In certain embodiments, the surfactant may be a quaternary ammonium compound, an amine oxide, an ionic or non-ionic surfactant, or any combination thereof. Suitable quaternary amine compounds include, but are not limited to, alkyl benzyl ammonium chloride, benzyl cocoalkyl($C_{12}$-$C_{18}$)dimethylammonium chloride, dicocoalkyl ($C_{12}$-$C_{18}$)dimethylammonium chloride, ditallow dimethylammonium chloride, di(hydrogenated tallow alkyl)dimethyl quaternary ammonium methyl chloride, methyl bis(2-hydroxyethyl cocoalkyl($C_{12}$-$C_{18}$) quaternary ammonium chloride, dimethyl(2-ethyl) tallow ammonium methyl sulfate, n-dodecylbenzyldimethylammonium chloride, n-octadecylbenzyldimethyl ammonium chloride, n-dodecyltrimethylammonium sulfate, soya alkyltrimethylammonium chloride, and hydrogenated tallow alkyl (2-ethylhyexyl) dimethyl quaternary ammonium methyl sulfate.

s. Additional Components

Corrosion inhibitor compositions made according to the invention may further include additional functional agents or additives that provide a beneficial property. For example, additional agents or additives may be selected from the group consisting of pH adjusters or other neutralizing agents, surfactants, emulsifiers, sequestrants, solubilizers, other lubricants, buffers, detergents, cleaning agent, rinse aid composition, secondary anti-corrosion agent, preservatives, binders, thickeners or other viscosity modifiers, processing aids, carriers, water-conditioning agents, foam inhibitors or foam generators, threshold agent or system, aesthetic enhancing agent (i.e., dye, odorant, perfume), other agents or additives suitable for formulation with a corrosion inhibitor composition and the like, and mixtures thereof. Additional agents or additives will vary according to the particular corrosion inhibitor composition being manufactured and its intend use.

3. METHODS OF USE

The compositions of the invention can be used in any industry where it is desirable to inhibit corrosion at a surface. The compositions can be used to inhibit corrosion of yellow metals, including yellow metals subjected to halogenation (e.g., chlorination) or halogen-containing agents.

The compositions can be used to inhibit corrosion of mild steel, including mild steel subjected to corrosive copper species.

The present compositions and methods are applicable to all industries that can employ water treatment processes. For example, the different types of industrial processes in which the compositions of the present invention can be applied generally include raw water processes, waste water processes, industrial water processes, municipal water treatment, food and beverage processes, pharmaceutical processes, electronic manufacturing, utility operations, pulp and paper processes, mining and mineral processes, transportation-related processes, textile processes, plating and metal working processes, laundry and cleaning processes, leather and tanning processes, and paint processes.

In particular, food and beverage processes can include, for example, dairy processes relating to the production of cream, low-fat milk, cheese, specialty milk products, protein isolates, lactose manufacture, whey, casein, fat separation, and brine recovery from salting cheese. Uses relating to the beverage industry include, for example, fruit juice clarification, concentration or deacidification, alcoholic beverage clarification, alcohol removal for low-alcohol content beverages, process water; and uses relating to sugar refining, vegetable protein processing, vegetable oil production/processing, wet milling of grain, animal processing (e.g., red meat, eggs, gelatin, fish and poultry), reclamation of wash waters, food processing waste and the like.

The compositions are useful for corrosion inhibition of containers, processing facilities, or equipment in the food service or food processing industries. The compositions have particular value for use on food packaging materials and equipment, and especially for cold or hot aseptic packaging. Examples of process facilities in which the compositions can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The compositions can be used to inhibit corrosion in tanks, lines, pumps, and other equipment used for the manufacture and storage of soft drink materials, and also used in the bottling or containers for the beverages.

The compositions can be used on or in industrial equipment and in industrial process streams such as heaters, cooling towers, boilers, retort waters, rinse waters, aseptic packaging wash waters, and the like. The compositions can be used to treat surfaces in recreational waters such as in pools, spas, recreational flumes and water slides, fountains, and the like.

The compositions can be used to inhibit the corrosion of metal surfaces contacted with cleaners found in janitorial and/or housekeeping applications, food processing equipment and/or plant applications, and in laundry applications. For example, the corrosion of washers, such as tunnel washers for washing textiles, may be inhibited according to methods disclosed herein.

The compositions can be used or applied in combination with low temperature dish and/or warewash sanitizing final rinse, toilet bowl cleaners, and laundry bleaches. The compositions and methods can be used to treat metal surfaces, such as ware, cleaned and/or sanitized with corrosive sources.

The compositions and methods disclosed herein can be used to protect surfaces from corrosion caused by hypochlorite bleach. A method may include providing the corrosion inhibitor composition to a surface treated with a hypochlorite solution in order to inhibit corrosion caused by the hypochlorite solution. The method may include preparing an aqueous use composition of the present corrosion inhibitor composition. The method may further include contacting a surface, such as a hard metal surface, in need of corrosion inhibition due to contact with a hypochlorite solution.

Examples of industrial water uses as applied to the present invention include, for example, boiler water production, process water purification and recycle/reuse, softening of raw water, treatment of cooling water blow-down, reclamation of water from papermaking processes, desalination of sea and brackish water for industrial and municipal use, drinking/raw/surface water purification including, for example, the use of membranes to exclude harmful microorganisms from drinking water, polishing of softened water, membrane bio-reactors, mining and mineral process waters.

Examples of waste water treatment applications with respect to the compositions and methods of this invention include, for example, industrial waste water treatment, biological-waste treatment systems, removal of heavy metal contaminants, polishing of tertiary effluent water, oily waste waters, transportation related processes (e.g., tank car wash water), textile waste (e.g., dye, adhesives, size, oils for wool scouring, fabric finishing oils), plating and metal working waste, laundries, printing, leather and tanning, pulp and paper (e.g., color removal, concentration of dilute spent sulfite liquor, lignin recovery, recovery of paper coatings), chemicals (e.g., emulsions, latex, pigments, paints, chemical reaction by-products), and municipal waste water treatment (e.g., sewage, industrial waste).

Other examples of industrial applications of the present invention include, for example, semiconductor rinse water processes, production of water for injection, pharmaceutical water including water used in enzyme production/recovery and product formulation, and electro-coat paint processing.

The compositions of the invention may be used for inhibiting corrosion in coal-based power plant applications. In particular, the compositions may be used in cooling water applications relating to thermoelectric power plants. The compositions may be used for inhibiting corrosion by treating a cooling liquid (e.g., water) with an effective amount of a composition of the invention, as described herein.

The compositions of the invention may be used for inhibiting corrosion in oil and gas applications. The compositions may be used for inhibiting corrosion by treating a gas or liquid stream with an effective amount of a compound or composition of the invention, as described herein.

In certain embodiments, the compositions can be used in water systems, condensate/oil systems/gas systems, or any combination thereof. In certain embodiments, the compositions can be applied to a gas or liquid produced or used in the production, transportation, storage, and/or separation of crude oil or natural gas. In certain embodiments, the compositions can be applied to a gas or liquid used or produced in a coal-fired process, such as a coal-fired power plant. In certain embodiments, the compositions can be applied to a gas or liquid produced or used in a waste-water process, a farm, a slaughter house, a land-fill, a municipality wastewater plant, a coking coal process, or a biofuel process.

A fluid to which the compositions may be introduced may be an aqueous medium. In certain embodiments, the aqueous medium may comprise water, gas, and optionally liquid hydrocarbon. A fluid to which the compositions may be introduced may be a liquid hydrocarbon. The liquid hydrocarbon may be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. In certain embodiments, the fluid or gas may be a refined hydrocarbon product.

A fluid or gas treated with a composition of the invention may be at any selected temperature, such as ambient temperature or an elevated temperature. In certain embodiments, the fluid (e.g., liquid hydrocarbon) or gas may be at a temperature of from about 40° C. to about 250° C. In certain embodiments, the fluid or gas may be at a temperature of from −50° C. to 300° C., 0° C. to 200° C., 10° C. to 100° C., or 20° C. to 90° C. In certain embodiments, the fluid or gas may be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. In certain embodiments, the fluid or gas may be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compositions of the invention may be added to a fluid at various levels of water cut. For example, the water cut may be from 0% to 100% volume/volume (v/v), from 1% to 80% v/v, or from 1% to 60% v/v. The fluid can be an aqueous medium that contains various levels of salinity. In one embodiment, the fluid may have a salinity of 0% to 25%, about 1% to 24%, or about 10% to 25% weight/weight (w/w) total dissolved solids (TDS).

The fluid or gas in which the compositions of the invention are introduced may be contained in and/or exposed to many different types of apparatuses. For example, the fluid or gas may be contained in an apparatus that transports fluid or gas from one point to another, such as an oil and/or gas pipeline. In certain embodiments, the apparatus may be part of an oil and/or gas refinery, such as a pipeline, a separation vessel, a dehydration unit, or a gas line. The fluid may be contained in and/or exposed to an apparatus used in oil extraction and/or production, such as a wellhead. The apparatus may be part of a coal-fired power plant. The apparatus may be a scrubber (e.g., a wet flue gas desulfurizer, a spray dry absorber, a dry sorbent injector, a spray tower, a contact or bubble tower, or the like). The apparatus may be a cooling tower. The apparatus may be a cargo vessel, a storage vessel, a holding tank, or a pipeline connecting the tanks, vessels, or processing units. In certain embodiments, the fluid or gas may be contained in water systems, condensate/oil systems/gas systems, or any combination thereof.

The compositions of the invention may be introduced into a fluid or gas by any appropriate method for ensuring dispersal through the fluid or gas. In certain embodiments, the inhibitor composition is added at a point in a flow line upstream from the point at which corrosion prevention is desired. The compositions may be injected using mechanical equipment such as chemical injection pumps, piping tees, injection fittings, atomizers, quills, and the like. The compositions of the invention may be introduced with or without one or more additional polar or non-polar solvents depending upon the application and requirements. In certain embodiments, the compositions of the invention may be pumped into an oil and/or gas pipeline using an umbilical line. In certain embodiments, capillary injection systems can be used to deliver the compositions to a selected fluid. In certain embodiments, the compositions can be introduced into a liquid and mixed. In certain embodiments, the compositions can be injected into a gas stream as an aqueous or nonaqueous solution, mixture, or slurry. In certain embodiments, the fluid or gas may be passed through an absorption tower comprising a composition of the invention.

The corrosion inhibitor compositions may be dispensed using a spray-type dispenser, such as that disclosed in U.S. Pat. Nos. 4,826,661, 4,690,305, 4,687,121, 4,426,362 and in U.S. Pat. Nos. Re 32,763 and 32,818, the disclosures of which are incorporated by reference herein. A spray-type dispenser functions by impinging a water spray upon an exposed surface of a composition to dissolve a portion of the composition, and then immediately directing the concentrate solution including the composition out of the dispenser to a storage reservoir or directly to a point of use.

In certain embodiments, the compositions may be dispensed by immersing either intermittently or continuously in water. The composition can then dissolve, for example, at a controlled or predetermined rate. The rate can be effective to maintain a concentration of dissolved agent that is effective for use according to the methods disclosed herein.

The compositions may be applied to a fluid or gas to provide any selected concentration. In practice, the compositions of the invention are typically added to a flow line to provide an effective treating dose of the described compounds or compositions from about 0.01 to about 5,000 ppm. In certain embodiments, the compositions may be applied to a fluid or gas to provide an actives concentration of about 1 parts per million (ppm) to about 1,000,000 ppm, about 1 parts per million (ppm) to about 100,000 ppm, or about 10 ppm to about 75,000 ppm. The compositions may be applied to a fluid to provide an actives concentration of about 100 ppm to about 10,000 ppm, about 200 ppm to about 8,000 ppm, or about 500 ppm to about 6,000 ppm. In certain embodiments, the compositions are applied to a fluid or gas to provide an actives concentration of 0.1 ppm, 0.5 ppm, 1 ppm, 2 ppm, 5 ppm, 10 ppm, 20 ppm, 100 ppm, 200 ppm, 500 ppm, 1,000 ppm, 5,000 ppm, 10,000 ppm, 20,000 ppm, or greater. In certain embodiments, the compositions are applied to a fluid or gas to provide an actives concentration of 0.125 ppm, 0.25 ppm, 0.625 ppm, 1 ppm, 1.25 ppm, 2.5 ppm, 5 ppm, 10 ppm, or 20 ppm. Each system may have its own dose level requirements, and the effective dose level of a composition to sufficiently reduce the rate of corrosion may vary with the system in which it is used.

The compositions may be applied continuously, in batch, or a combination thereof. In certain embodiments, the composition doses may be continuous to prevent corrosion. In certain embodiments, the composition doses may be intermittent (i.e., batch treatment). In a further embodiment, the composition doses may be continuous/maintained and/or intermittent to inhibit corrosion. Dosage rates for continuous treatments typically range from about 10 to about 500 ppm, or about 10 to about 200 ppm. Dosage rates for batch treatments typically range from about 10 to about 400,000 ppm, or about 10 to about 20,000 ppm. In certain embodiments, the composition may be applied as a pill to a pipeline, providing a high dose (e.g., 20,000 ppm) of the composition.

The flow rate of a flow line in which the composition is used may be between 0 and 100 feet per second, or between 0.1 and 50 feet per second. In some cases, the compositions may be formulated with water in order to facilitate addition to the flow line.

4. EXAMPLES

The foregoing may be better understood by reference to the following examples, which are presented for purposes of illustration and are not intended to limit the scope of the invention.

Compounds of the invention were synthesized with high purity and good yield. The reaction methods were fine-tuned to provide good conversion with less byproduct formation.

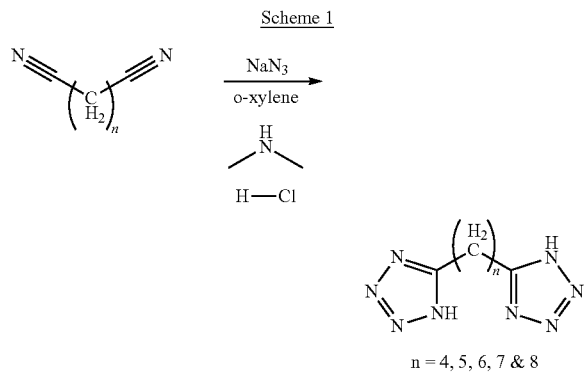

A general reaction scheme for preparing compounds of the invention is shown in Scheme 1. Sodium azide was added to dinitriles with dimethyl amine hydrochloride as a catalyst, using o-xylene as a solvent with a reaction time of 2 to 8 hours. The reaction proceeds via a traditional [2+3] mechanism and then undergoes 1,5-cyclization to give ditetrazole/tritetrazole product(s).

Example 1

1,4-di(1H-tetrazol-5-yl)butane (BDTZ)

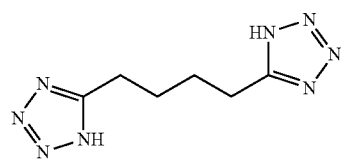 [SMILES: C(CCc1nnn[nH]1)Cc1nnn[nH]1]

To a two-neck 250 ml round bottom flask fitted with reflux condenser was added sodium azide (2.86 g, 44 mmol), dimethylamine hydrochloride (3.587 g, 44 mmol) and 20 ml o-xylene, and stirred (@1000 rpm). To this mixture at 70° C. was added adiponitrile (2.275 ml, 20 mmol). The reaction mixture was heated at 120° C. for 2-4 hrs and checked for consumption of starting material using thin layer chromatography. Once starting material was consumed the reaction mixture was a thick pasty mixture, and was cooled to room temperature. To the mixture was added 50 ml of RO water, and was stirred well to separate into two layers. The aqueous layer was separated and acidified to pH 1 with 10 ml of (1:1) aqueous diluted HCl with vigorous stirring to give pure product BDTZ. The white solid was then isolated by vacuum filtration (1 bar), dried in the oven at 50° C. for 24 hrs, to give 3.4983 g of crude product (90.16% yield). 1,4-di(1H-tetrazol-5-yl)butane (BDTZ): mp 201.82° C.; $^1$H-NMR (DMSO-d6) 2.95 (4H, t) and 2.13(2H, q); $^{13}$C NMR 155.45 (br), 24.87 and 22.23 (aliphatic C); FTIR 1455 (C—H), 1285 (N—N=N—), 1108 and 1140 (tetrazole ring) cm$^{-1}$; MS+m/z, 195, 170, 198, 152 and 197.

Example 2

1,6-di(1H-tetrazol-5-yl)hexane (HDTZ)

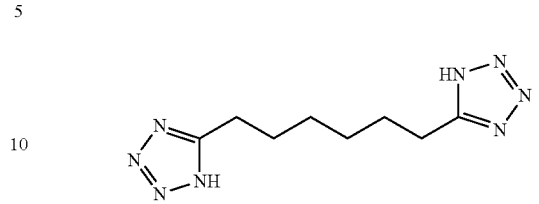

To a two-neck 250 ml round bottom flask fitted with reflux condenser was added sodium azide (2.86 g, 44 mmol), dimethylamine hydrochloride (3.587 g, 44 mmol) and 20 ml o-xylene, and stirred (@1000 rpm). To this mixture at 70° C. was added 1,6-dicyanohexane (2.855 ml, 20 mmol). The reaction mixture was heated at 120° C. for 4 hrs and checked for consumption of starting material using thin layer chromatography. Once starting material was consumed the reaction mixture was a thick pasty mixture, and was cooled to room temperature. To the mixture was added 50 ml of RO water, and was stirred well to separate into two layers. The aqueous layer was separated and acidified to pH 1 with 10 ml of (1:1) aqueous diluted HCl with vigorous stirring to give pure product HDTZ. The pale white solid was then isolated by vacuum filtration (1 bar), dried in the oven at 50° C. for 24 hrs, to give 3.8009 g of crude product (91.36% yield). 1,6-di(1H-tetrazol-5-yl)hexane (HDTZ): mp 183.75° C.; $^1$H-NMR (DMSO-d6) 2.95 (4H, t), 1.65 (4H, q) and 1.3 (4H, q); $^{13}$C NMR 155.45 (br), 26.5, 27.5 (methylene C) and 22.23 (aliphatic C); FTIR 1455 (C—H), 1285 (N—N=N—), 1108 and 1140 (tetrazole ring) cm$^{-1}$; MS+m/z, 223, 198, 226, 180 and 237.

Example 3

1,7-di(1H-tetrazol-5-yl)heptane (HeDTZ)

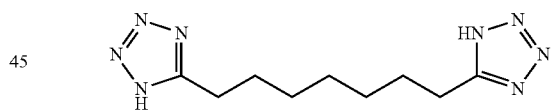

To a two-neck 250 ml round bottom flask fitted with reflux condenser was added sodium azide (2.86 g, 44 mmol), dimethylamine hydrochloride (3.587 g, 44 mmol) and 20 ml o-xylene, and stirred (@1000 rpm). To this mixture at 70° C. was added Azelanitrile (3.255 ml, 20 mmol). The reaction mixture was heated at 120° C. for 4 hrs and checked for consumption of starting material using thin layer chromatography. Once starting material was consumed the reaction mixture was a thick pasty mixture, and was cooled to room temperature. To the mixture was added 50 ml of RO water, and was stirred well to separate into two layers. The aqueous layer was separated and acidified to pH 1 with 10 ml of (1:1) aqueous diluted HCl with vigorous stirring to give pure product HeDTZ. The pale white solid was then isolated by vacuum filtration (1 bar), dried in the oven at 50° C. for 24 hrs, to give 3.7180 g of crude product (83.74% yield). 1,7-di(1H-tetrazol-5-yl)heptane (HeDTZ): mp 144.19° C.; $^1$H-NMR (DMSO-d6) 2.85 (4H, t), 1.65 (4H, q) and 1.3 (6H, q); $^{13}$C NMR 155.45 (br), 26.8, 27.9, 28.1 (methylene C)

and 22.5 (aliphatic C); FTIR 1455 (C—H), 1285 (N—N≡N—), 1108 and 1140 (tetrazole ring) cm$^{-1}$; MS+m/z, 237, 212, 240, 194 and 251.

Example 4

1,8-di(1H-tetrazol-5-yl)octane (ODTZ)

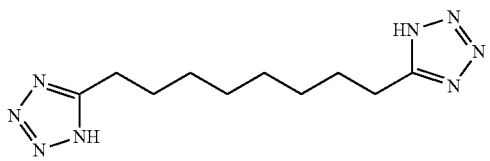 [SMILES: C(CCCCc1nnn[nH]1)CCCc1nnn[nH]1]

To a two-neck 250 ml round bottom flask fitted with reflux condenser was added sodium azide (2.86 g, 44 mmol), dimethylamine hydrochloride (3.587 g, 44 mmol) and 20 ml o-xylene, and stirred (@1000 rpm). To this mixture at 70° C. was added Sebaconitrile (3.6095 ml, 20 mmol). The reaction mixture was heated at 120° C. for 4 hours and checked for consumption of starting material using thin layer chromatography. Once starting material was consumed the reaction mixture was a thick pasty mixture, and was cooled to room temperature. To the mixture was added 50 ml of RO water, and was stirred well to separate into two layers. The aqueous layer was separated and acidified to pH 1 with 10 ml of (1:1) aqueous diluted HCl with vigorous stirring to give pure product ODTZ. The pale white solid was then isolated by vacuum filtration (1 bar), dried in the oven at 50° C. for 24 hrs, to give 3.820 g of crude product (81.27% yield). 1,8-di(1H-tetrazol-5-yl)heptane (ODTZ): mp 139.12° C.; $^1$H-NMR (DMSO-d6) 2.85 (4H, t), 1.65 (4H, q) and 1.25 (8H, q); $^{13}$C NMR 155.45 (br), 26.8, 28.1, 28.2(methylene C) and 22.5 (aliphatic C); FTIR 1455 (C—H), 1285 (N—N≡N—), 1108 and 1140 (tetrazole ring) cm$^{-1}$; MS+m/z, 251, 226, 254, 208, 265, 279 and 236.

Example 5

5,5',5''-(hexane-1,3,6-triyl)tris(1H-tetrazole) (TCH-TZ)

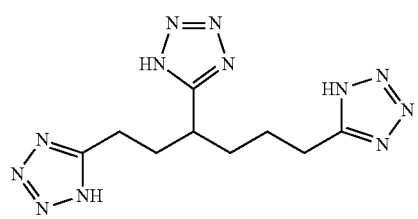 [SMILES: C(Cc1nnn[nH]1)CC(CCc1nnn[nH]1)c1nnn[nH]1]

To a two-neck 250 ml round bottom flask fitted with reflux condenser was added sodium azide (4.550 g, 70 mmol), dimethylamine hydrochloride (5.707 g, 70 mmol) and 20 ml o-xylene, and stirred (@1000 rpm). To this mixture at 70° C. was added 1,3,6-tricyanohexane (3.224 ml, 20 mmol). The reaction mixture was heated at 120° C. for 4 hrs and checked for consumption of starting material using thin layer chromatography. Once starting material was consumed the reaction mixture was a thick pasty mixture, and was cooled to room temperature. To the mixture was added 50 ml of RO water, and was stirred well to separate into two layers. The aqueous layer was separated and acidified to pH 1 with 10 ml of (1:1) aqueous diluted HCl with vigorous stirring to give pure product TCH-TZ. The pale white solid was then isolated by vacuum filtration (1 bar), dried in the oven at 50° C. for 24 hrs, to give 4.7810 g of crude product (82.46% yield). 5,5',5''-(hexane-1,3,6-triyl)tris(1H-tetrazole) (TCH-TZ): mp 219.62° C.; $^{13}$C NMR 155.45 (br), 22.3, 24.2, 30.6, 32.4, 33.6 (methylene C) and 20.4 (aliphatic C); FTIR 1455 (C—H), 1285 (N—N≡N—), 1108 and 1140 (tetrazole ring) cm$^{-1}$; MS+m/z, 291, 253, 248, 238, 205, 150, and 135.

To illustrate the advantages of the compounds and compositions of the invention, tetrazole-based compositions were prepared and evaluated.

Example 6

Formulate at Neutral pH

The solubility of 2% solutions of compounds of the invention were determined at various pH. The solutions were prepared by dissolving 2 g of the tetrazole compounds in 100 ml of Reverse Osmosis (RO) water. The preparation was divided into 10 portions. The pH of each aliquot was adjusted by adding 1N sodium hydroxide. The turbidity was determined with a turbidity meter. The data of the turbidity reading verses the pH are plotted in FIGS. 1-6.

The data shows that all the selected tetrazole derivatives are soluble at high concentrations (2%) over a wide range of pH from 6.5 to 14. The BDTZ solution remained clear for all measurements above a pH of 5.6. The solutions of HDTZ, HeDTZ, ODTZ, and TCH-TZ remained clear for all measurements above a pH of 6.5. In contrast, the solubility data for tolyltriazole (TT) shows that TT is soluble only at a pH above 11.5. To get a clear TT solution, the pH should be adjusted to 12.0; this pH range is basic in nature and handling of this product needs more safety than the disclosed tetrazole compounds.

The solubility of tetrazoles at neutral pH allows their formulation into corrosion inhibitor compositions at a neutral pH. This is a significant advantage in terms of safety, product image, cost and manufacturing compared to products requiring a pH outside of neutral.

Example 7

Low Toxicity/Green Alternative

Figure 7:
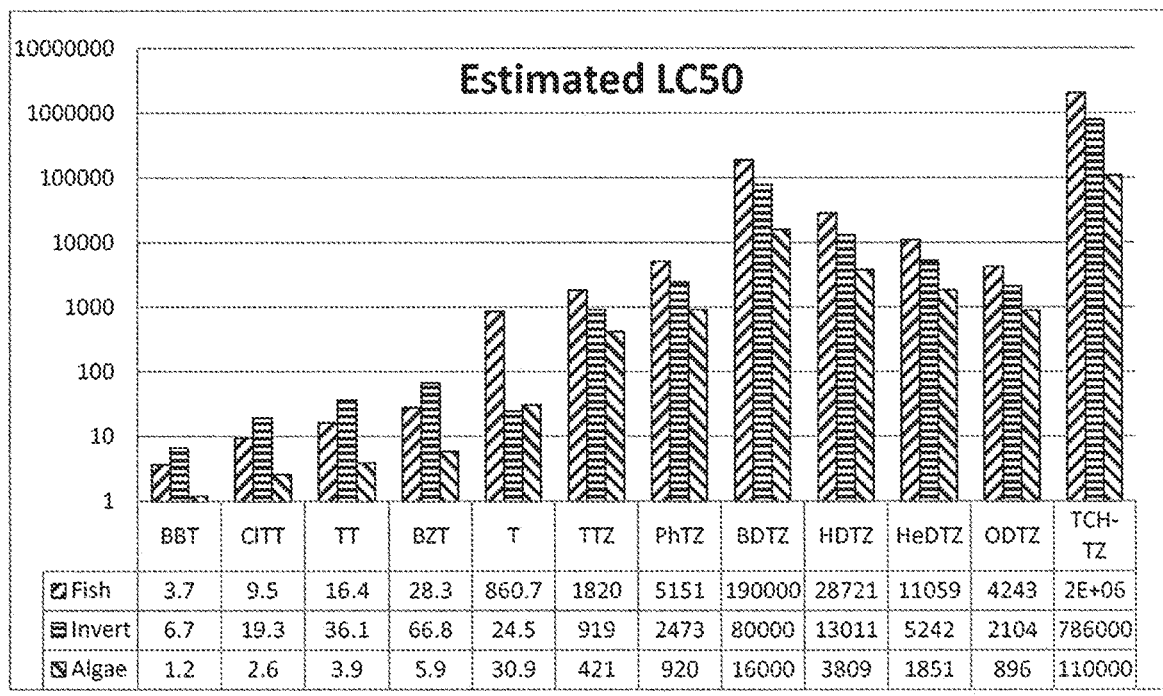
FIG. 7 depicts estimated LC50 toxicity values of tetrazole and triazole compounds.
Figure 8:
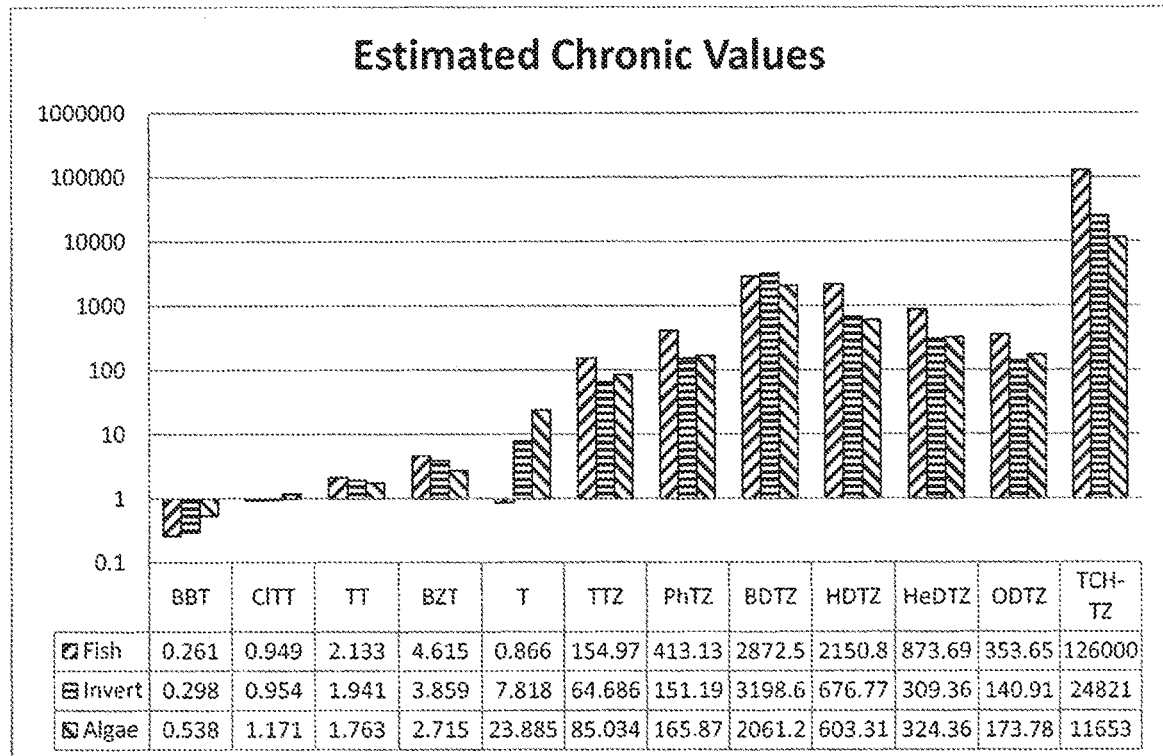
FIG. 8 depicts estimated chronic toxicity values of tetrazole and triazole compounds.

An Ecotox modeling software was used to estimate the LC50 and chronic values for the disclosed tetrazoles in fish, invertebrates, and algae. To validate results, tetrazoles were screened using PBT profiler, resulting in a similar estimation, although PBT profiler predicts chronic Ecotox. ECOSAR predicts both acute (FIG. 7) and chronic (FIG. 8) values. As shown in FIGS. 7 and 8, tetrazoles highlight the potential to provide an environmentally friendly alternative to standard technology. As an additional toxicological advantage, the disclosed tetrazoles during physical experiments showed an affinity to append with Cu$^{2+}$ species, which are toxic in water. Data supporting this interaction of tetrazoles with Cu$^{2+}$ is illustrated below.

A composition of the invention including a BDTZ tetrazole component was evaluated using the *Pimephales promelas* 96-Hour Definitive Toxicity Test. *Pimephales promelas* used to initiate this test were obtained from in-house cultures and were 1 to 14 days old at test initiation. Test organisms were maintained in 100 percent control water (reconstituted moderately hard water) prior to test initiation. The 96-Hour Definitive Test was conducted using 300 to 500 milliliter (mL) disposable polypropylene containers containing 250 ml of control water or appropriate test solution. Ten test organisms were randomly introduced into each test chamber with two replicate chambers per treatment. Each *Pimephales promelas* test chamber was fed 0.1 mL of a concentrated suspension of less than 24-hour old live brine shrimp nauplii (*Artemia* sp.) several hours prior to the 48-hour testing period.

At the 48-hour testing period, test solutions were renewed by replacing approximately 90 percent of the old solution with fresh control water or appropriate test solution. Prior to renewal of test solutions, uneaten and dead brine shrimp, along with other debris, were removed from the bottom of the test chambers. Organism survival was determined daily by enumerating live *Pimephales promelas* in each test chamber. Survival was defined as any body movement after gentle prodding.

The test was conducted at a temperature of 20±1° C. under fluorescent lighting with a photoperiod of 16 hours light and 8 hours dark. Water quality measurements were performed on all control and test solutions prior to test initiation and on selected treatments daily thereafter.

Following termination of the 96-Hour Definitive Test, No Observed Effect Concentration (NOEC) and a 96-hour LC50 with corresponding 95 percent confidence interval was calculated, where possible. The NOEC value was determined using the statistically appropriate method. The LC50 value estimate was determined by using one of the following statistical methods: graphical, Spearman-Karber, Trimmed Spearman-Karber, or Probit. The method selected for reporting test results was determined by the characteristics of the data; that is, the presence or absence of 0 and 100 percent mortality and the number of concentrations in which mortalities between 0 and 100 percent occurred. All statistical analyses were performed using the CETIS™ Version 1.8.5.4 software program.

The reference toxicant, sodium chloride, was used to monitor the sensitivity of the test organisms and the precision of the testing procedure. Acute reference toxicant tests are performed at least monthly and the resulting LC50 values are plotted to determine if the results are within prescribed limits. If the LC50 of a particular reference toxicant test does not fall within the expected range of ±two standard deviations from the mean for a given test organism, the sensitivity of that organism and the overall credibility of the test system is suspect.

Table 1 shows the data summary and the test results of the toxicity tests for a composition of BDTZ.

TABLE 1

| DATA SUMMARY | |
|---|---|
| Concentration (mg/L as nominal) | Survival (%) |
| Control | 100 |
| 625 | 100 |
| 1,250 | 100 |
| 2,500 | 100 |
| 5,000 | 100 |
| 10,000 | 100 |
| TEST RESULTS | |
| NOEC | 10,000 mg/L |
| 96-hour LC$_{50}$ | >10,000 mg/L |

Example 8

Corrosion Inhibition Efficacy with and without Chlorination

Figure 9:
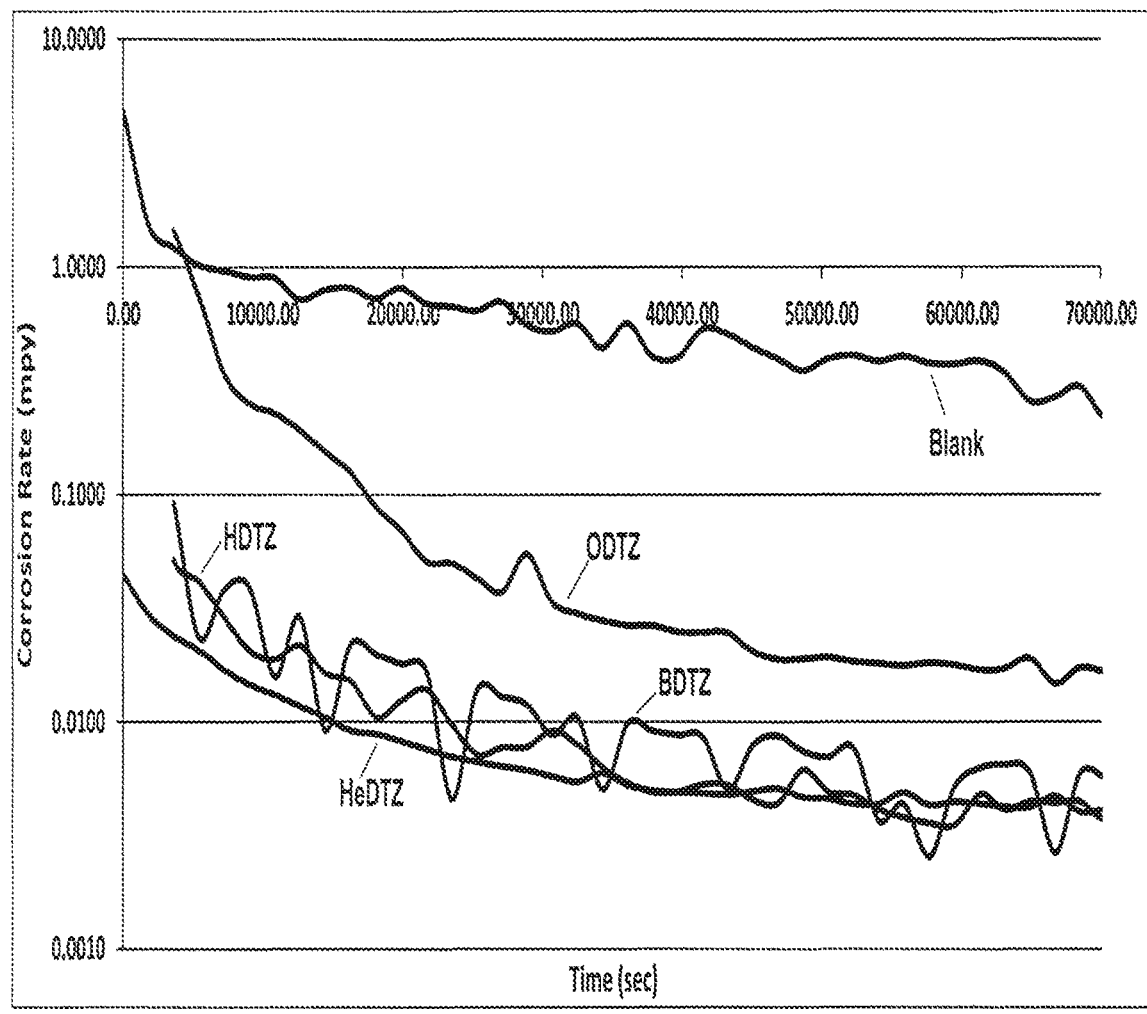
FIG. 9 depicts inhibitor effect on copper corrosion rate (mpy) versus time in the absence of bleach.
Figure 10:
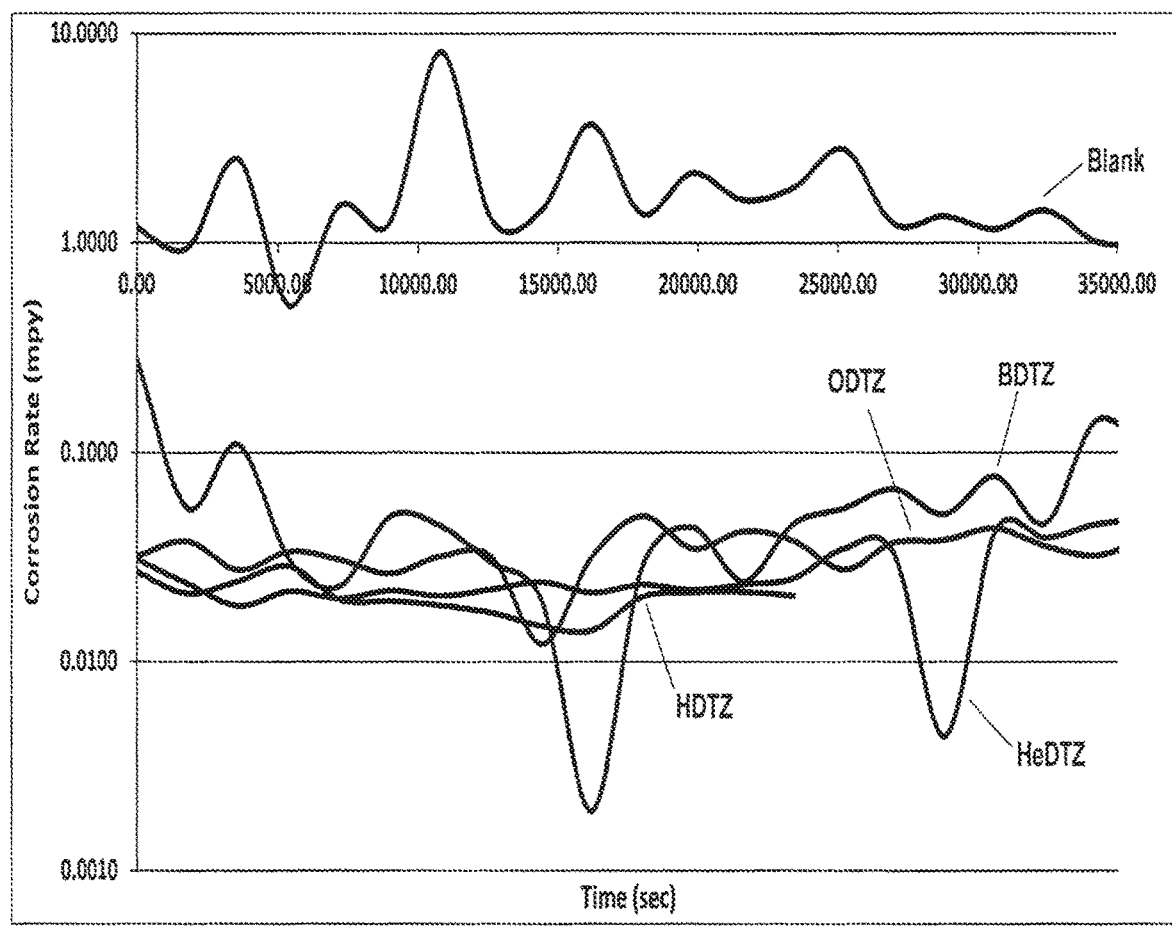
FIG. 10 depicts inhibitor effect on copper corrosion rate (mpy) versus time in the presence of bleach.
Figure 11:
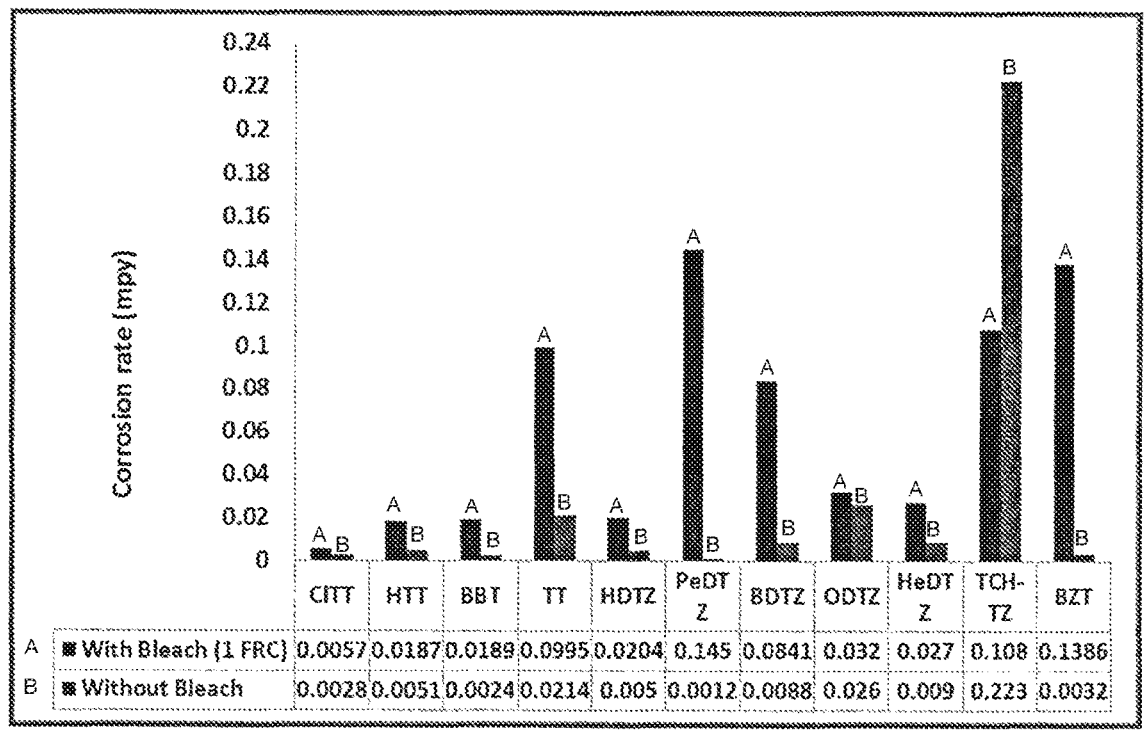
FIG. 11 depicts inhibitor effect on copper corrosion rate (mpy).

HDTZ, HeDTZ, ODTZ, and BDTZ have the advantage of being able to inhibit copper corrosion in a cooling water environment with and without the presence of bleach. The corrosion rate of the blank (without inhibitor), HDTZ, HeDTZ, and ODTZ in the absence and presence of bleach (1 ppm FRC) is presented in the FIGS. 9-10. Table 2 and FIG. 11 summarize the average corrosion rates of all the inhibitors. The experimental conditions were similar for all the corrosion tests, each having an inhibitor concentration of 5 ppm. The corrosion rates in the absence of bleach are within the corrosion rate limit for all the inhibitors. Similarly, the corrosion rates in the presence of bleach (1 ppm FRC) were also within the corrosion rate limit (<0.3 mpy). From the corrosion data, the film formed has the ability to prevent the corrosion even by the attack of the bleach at 1 ppm FRC. The average corrosion rates for the individual inhibitors were plotted in the presence and absence of the bleach.

TABLE 2

| Corrosion rate comparison of inhibitors | | |
|---|---|---|
| | Corrosion Rate (mpy) | |
| | with Bleach (1 FRC) | without Bleach |
| CITT | 0.0057 | 0.0028 |
| HTT | 0.0187 | 0.0051 |
| BBT | 0.0189 | 0.0024 |
| TT | 0.0995 | 0.0214 |
| HDTZ | 0.0204 | 0.005 |
| PeDTZ | 0.145 | 0.0012 |
| BDTZ | 0.0841 | 0.0088 |
| ODTZ | 0.032 | 0.026 |
| HeDTZ | 0.027 | 0.009 |
| TCH-TZ | 0.108 | 0.223 |
| BZT | 0.1386 | 0.0032 |

Example 9

Interaction with $Cu^{2+}$

Tetrazoles have a strong inclination to interact with $Cu^{2+}$ species. This phenomenon provides a unique avenue of synthesizing a complimentary formulation with $Cu^{1+}$ inhibitors (e.g., triazole inhibitors) that can result in corrosion protection against both $Cu^{1-}$ and $Cu^{2+}$ species, thus providing inhibition coverage over a wider ORP domain. Interaction of tetrazoles with $Cu^{2+}$ would also result in improved inhibition compared to other $Cu^{1+}$ inhibitors in the industry since the inhibitor will be able to provide the additional benefit of protecting mild steel against corrosion.

Figure 12:
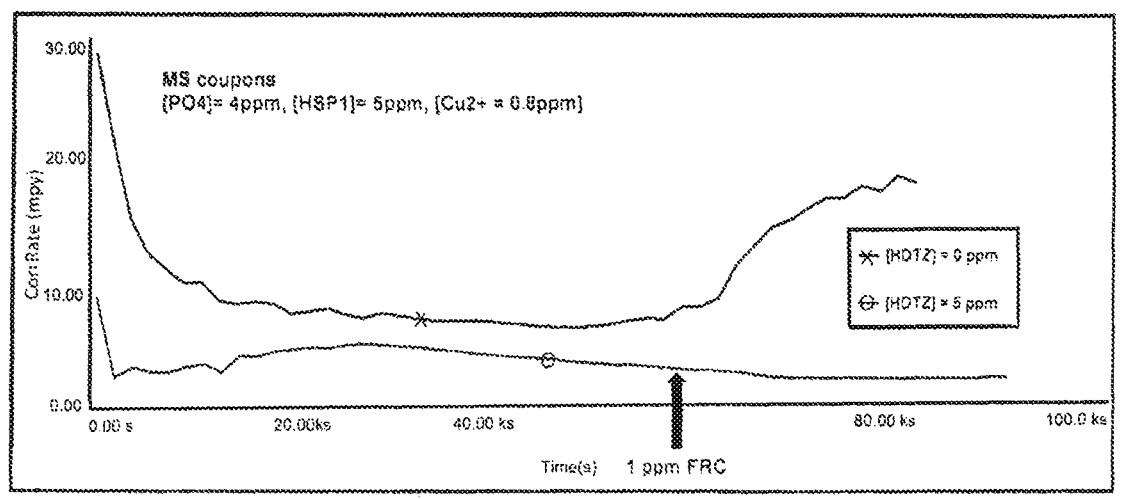
FIG. 12 depicts inhibitor effect on corrosion rate of mild steel.

Tetrazoles disclosed herein have a positive effect on mild steel corrosion. Addition of HDTZ seems to stabilize the corrosion rate, whereas the corrosion rate increases regularly without the HDTZ. The proposed mechanism of action is suspected to be indirect: the likely interpretation is that HDTZ inactivates $Cu^{2+}$ in solution preventing the occurrence of galvanic cells on the coupon surface (lower corrosion rate), which could grow with time (stabilization of the corrosion rate). The chlorination does not have an impact on the mild steel corrosion (FIG. 12).

Example 10

Bulk Halogen Stability

Bulk halogen stability tests were conducted with the tetrazoles BDTZ, HDTZ, and ODTZ. The stability of the tetrazoles was compared with tolyltriazole.

The concentration of the tetrazoles was measured using a HPLC method. The oxidizing biocides used in this study were 1) bleach (sodium hypochlorite), 2) STABREX®, and 3) ActiBrom®. The procedure to conduct the tests is as follows: 1) Prepare a solution of synthetic cooling water—150 ppm Ca/75 ppm Mg/110 ppm M alkalinity, all as $CaCO_3$ and 15 ppm 2-phosphonobutane-1,2,4-tricarboxylic acid (PBTC) to stabilize the water and prevent $CaCO_3$ precipitation. Adjust the pH of the water as desired with $H_2SO_4$ or NaOH. If testing for bleach stability, use pH 7.2) Prepare 3 ppm inhibitor solution using the above synthetic water. Take out 100 ml of inhibitor solution in an amber colored bottle and add biocides individually at two different concentrations (1 and 5 ppm). Biocide concentrations were measured using the DPD test method using a DR2800 spectrophotometer. Keep a control which has no biocide, only the inhibitor in the synthetic water. 3) Cap the bottles and place in a water bath heated to 100° F./38° C. for three hours. 4) Check FRC and TRO levels intermittently (~every hour) by the DPD test to ensure that there is still an adequate residual. If the residual is depleted, add the appropriate amount of OB to the sample bottle. After three hours, take the samples out of the bath and reduce the residual OB in solution. This can be done with a couple of drops of ~5000 ppm erythorbic acid solution. Check that the residual is reduced, using the DPD test. When the samples have reached room temperature, determine the concentration of the tetrazole in the control sample and in each of the reacted samples using HPLC. A percent consumption can be calculated from these concentrations:

$$\% \text{ consumption} = \frac{[\text{control}] - [\text{reacted sample}]}{[\text{control}]}$$

Table 3 shows that BDTZ, HDTZ, and ODTZ are stable in the presence of different oxidizing biocides. Tolyltriazole showed degradation in the presence of Actibrom at 1 and 5 ppm. Tetrazoles (BDTZ, HDTZ and ODTZ) were stable in the presence of Actibrom, STABREX and bleach, e.g., the % loss due to oxidizing biocides was <2.7%.

TABLE 3

Halogen stability of inhibitors

|  | HDTZ (% loss of inhibitor) | BDTZ (% loss of inhibitor) | ODTZ (% loss of inhibitor) | TT (% loss of inhibitor) |
| --- | --- | --- | --- | --- |
| 1 ppm Bleach | 2.6 | 0.9 | 2.6 | 2.1 |
| 5 ppm Bleach | 1.0 | 2.5 | 2.6 | 5.6 |
| 1 ppm STABREX | 0.0 | 1.6 | 1.6 | 7.6 |
| 5 ppm STABREX | 0.6 | 0.3 | 2.6 | 20.8 |
| 1 ppm ActiBrom | 1.0 | 0.0 | 0.0 | 100.0 |
| 5 ppm ActiBrom | 2.2 | 1.9 | 1.3 | 100.0 |

Example 11

Corrosion Inhibitor Compositions

BDTZ, HDTZ, HeDTZ, ODTZ and TCH-TZ were formulated as single drum products at neutral pH. The formulations are safe to handle and transport due to the neutral pH. A maximum concentration of tetrazole compound was used to prepare the single product formulations. The formulations may be combined with cooling water treatment programs.

The tetrazoles (BDTZ, HDTZ, HeDTZ, ODTZ and TCH-TZ) were dissolved in sodium hydroxide solutions to make the tetrazoles soluble. The tetrazole compounds were prepared at 40-42% concentration in an aqueous medium and the pH for the solutions was at 7.00. Table 4 provides the amount of tetrazole compound and sodium hydroxide added to prepare the single product formulations.

TABLE 4

Single product formulation compositions

|  | BDTZ | HDTZ | HeDTZ | ODTZ | TCH-TZ |
| --- | --- | --- | --- | --- | --- |
| tetrazole | 2.14 g | 2.14 g | 2.14 g | 2.14 g | 2.14 g |
| 40% NaOH | 2.6 ml | 2.4 ml | 2.5 ml | 2.8 ml | 2.8 ml |
| RO water | 2.4 ml | 2.6 ml | 2.5 ml | 2.5 ml | 2.5 ml |
| pH | 7.12 | 7.02 | 7.31 | 7.04 | 7.00 |
| % active | 42.8 | 42.8 | 42.8 | 40.38 | 40.38 |

A corrosion inhibitor composition including additional components was formulated, as shown in Table 5. In addition to the tetrazole, the composition includes water, a tracer, a scale inhibitor, a dispersant, an acid, and a base.

TABLE 5

Corrosion Inhibitor Composition

| Component | Amount (wt %) |
| --- | --- |
| Tetrazole | 1.46 |
| Water (Solvent) | 37.932 |
| Tracer | 1 |
| 31% PSO (Scale Inhibitor) | 14.49 |
| 45% $HSP_2$ (Dispersant) | 16.67 |
| 85% $H_3PO_4$ (Acid) | 5.468 |
| 45% KOH (Base) | 22.98 |

The compounds and compositions disclosed herein provide several advantages over the current market standard, azole-based formulations. In particular, the pH of the tetrazole-based formulations are about 7 versus the highly acidic pH of azole-based formulations. This provides an improved environmental and safety profile. Furthermore, no concentrated sulfuric acid is required during the manufacturing process, further providing a product with reduced toxicity to the manufacturer and user.

Other advantages include that the compounds and compositions conserve the ability to protect yellow metals; the products have an improved corrosion inhibitive effect on yellow metals under chlorination; the products limit galvanic corrosion on mild steel (pitting attack), especially under chlorination; and the yellow metal protection component of the formulations exhibits a lower free chlorine demand than current azole-based formulations.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. A composition for inhibiting corrosion at a surface, the composition comprising 1,7-di(1H-tetrazol-5-yl)heptane ("HeDTZ").

2. The composition of claim 1, wherein the composition comprises about 40% by weight of the HeDTZ.

3. The composition of claim 1, wherein the composition is a water-based composition having a pH of 6-12.

4. The composition of claim 1, further comprising one or more components, each component independently selected from the group consisting of:
 a solvent;
 a tracer;
 a scale inhibitor;
 a dispersant;
 an acid; and
 a base.

5. The composition of claim 1, further comprising a dispersant, the dispersant comprising a copolymer of acrylamido-methyl propane sulfonate and acrylic acid.

6. The composition of claim 1, further comprising a scale inhibitor, the scale inhibitor comprising phosphinosuccinate oligomers.

7. The composition of claim 6, further comprising a dispersant, the dispersant comprising a copolymer of acrylamido-methyl propane sulfonate and acrylic acid.

* * * * *

UNITED STATES PATENT AND TRADEMARK OFFICE
CERTIFICATE OF CORRECTION

PATENT NO. : 10,899,721 B2
APPLICATION NO. : 15/676086
DATED : January 26, 2021
INVENTOR(S) : Jothibasu Seetharaman et al.

Page 1 of 1

It is certified that error appears in the above-identified patent and that said Letters Patent is hereby corrected as shown below:

On the Title Page

Column 2, Line 5, Item (57) Abstract - Delete "admirality" and insert -- admiralty --.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*